(12) United States Patent
Ferguson

(10) Patent No.: US 8,212,677 B2
(45) Date of Patent: Jul. 3, 2012

(54) AUTOMATED MEDICATION MANAGEMENT SYSTEM AND METHOD FOR USE

(76) Inventor: Alexander Ferguson, Bethesda, MD (US)

( * ) Notice: Subject to any disclaimer, the term of this patent is extended or adjusted under 35 U.S.C. 154(b) by 402 days.

(21) Appl. No.: 12/030,155

(22) Filed: Feb. 12, 2008

(65) Prior Publication Data

US 2009/0167531 A1 Jul. 2, 2009

Related U.S. Application Data

(60) Provisional application No. 60/889,511, filed on Feb. 12, 2007.

(51) Int. Cl.
*G08B 13/14* (2006.01)
(52) U.S. Cl. ..................... 340/572.3; 340/10.1
(58) Field of Classification Search .............. 340/572.3
See application file for complete search history.

(56) References Cited

U.S. PATENT DOCUMENTS

| | | | |
|---|---|---|---|
| 6,851,615 B2 * | 2/2005 | Jones | 235/487 |
| 7,035,818 B1 * | 4/2006 | Bandy et al. | 705/28 |
| 7,652,575 B2 * | 1/2010 | Lyons et al. | 340/572.1 |
| 7,782,189 B2 * | 8/2010 | Spoonhower et al. | 340/539.12 |
| 7,812,706 B2 * | 10/2010 | Suzuki et al. | 340/10.1 |
| 2002/0036237 A1 * | 3/2002 | Atherton et al. | 235/492 |
| 2004/0008123 A1 * | 1/2004 | Carrender et al. | 340/825.49 |
| 2005/0240305 A1 * | 10/2005 | Bogash et al. | 700/242 |
| 2006/0220855 A1 * | 10/2006 | Hartmann et al. | 340/572.1 |
| 2006/0290471 A1 * | 12/2006 | Van Alstyne | 340/10.1 |
| 2007/0008121 A1 * | 1/2007 | Hart | 340/540 |
| 2007/0096906 A1 * | 5/2007 | Lyons et al. | 340/572.1 |
| 2007/0145130 A1 * | 6/2007 | Danilewitz | 235/385 |
| 2007/0150382 A1 * | 6/2007 | Danilewitz | 705/28 |
| 2007/0152822 A1 * | 7/2007 | Eren et al. | 340/572.1 |
| 2007/0229268 A1 * | 10/2007 | Swan et al. | 340/572.1 |
| 2007/0258048 A1 | 11/2007 | Pitchers | |
| 2007/0273504 A1 * | 11/2007 | Tran | 340/539.12 |
| 2008/0059228 A1 * | 3/2008 | Bossi et al. | 705/2 |
| 2009/0167531 A1 * | 7/2009 | Ferguson | 340/572.1 |
| 2010/0065647 A1 * | 3/2010 | Ritamaki et al. | 235/492 |
| 2010/0090802 A1 * | 4/2010 | Nilsson et al. | 340/10.1 |

OTHER PUBLICATIONS

PCT, International Search Report Mailed Jun. 19, 2009.
PCT International Preliminary Report on Patentability, Mailed Aug. 26, 2010.

* cited by examiner

*Primary Examiner* — Eric M Blount
(74) *Attorney, Agent, or Firm* — David P. Lentini

(57) ABSTRACT

Systems, apparatuses, and methods for tracking the status and use of packaged goods are provided. The systems of the invention coordinate various stakeholders, hardware devices, computer software systems, standards, methods, procedures, practices and their interconnection in ways that lead to greater efficiency, safety, and efficacy, along with potentially lower cost, and less waste in the delivery of packaged goods and their use. In one aspect a Medication Management System ("MMS") that tracks the status of packaged medications and patient compliance is also provided.

15 Claims, 20 Drawing Sheets

FIGURE 1b
(PRIOR ART)

AUTOMATED MEDICATION MANAGEMENT SYSTEM AND METHOD FOR USE

1 CROSS REFERENCE TO RELATED U.S. PATENT APPLICATIONS

This application claims priority under 35 U.S.C. § 119(e) to provisional U.S. Patent Application Ser. No. 60/889,511, titled Systems, Methods, and Software for Automated Medication Dispensing and Compliance, filed 12 Feb. 2007, the disclosure of which is incorporated herein by reference in its entirety and for all purposes.

2 COPYRIGHT NOTICE

A portion of the disclosure of this patent document may contain material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice shall apply to this document: Copyright 2008, Alexander Ferguson, All Rights Reserved.

3 BACKGROUND OF THE INVENTION

3.1 Field of the Invention

The present invention relates to the management of medication dispensing and use, and, more particularly, to the management of medication dispensing and use for individuals who have complex medication regimens. Still more particularly, the present invention provides systems, methods, and software for managing medication dispensing and use for individuals that are not sedentary or otherwise restricted in their activities in ways that are relevant to their medication regimen. The present invention has applications in the fields of medicine, pharmacology, computer science, and robotics.

3.2 The Related Art

Although modern medicine offers powerful remedies and palliatives for many diseases once considered to be death sentences, such as cancer, heart disease, and many bacterial infections, patients undergoing treatment must adhere to treatment regimens that often include precisely scheduled drug administration over a specific and often lengthy time period. During the treatment period, which can be life-long for diseases such as AIDS, the patient must also maintain awareness of any possible unwanted or dangerous side effects that could warrant change in the regimen. Variance from the regimen, i.e., a failure of compliance, can diminish the therapeutic effectiveness of the regimen and lead to delayed recovery, complications in treatment, or even thwart effective treatment all together, which not only prolongs a patient's suffering but increases the cost of care. In some cases, the compliance failure arises from a patient's failure to take enough medication—i.e., by under-medication. In other cases, especially concerning pain management, compliance failure can lead to drug addiction by over-medication. In still other cases, a patient can take the prescribed amount of medication, but outside of the prescribed schedule, leading to the patient's being under- or over-medicated at different times. Moreover, patients can be on treatment regimens for multiple diseases or conditions that lead to adverse drug interactions that can be fatal in some instances, see, e.g., (Nies 1975; Tollefson 1993; Dennehy, Kishi et al. 1996; Tamblyn 1996; Beyth and Shorr 1999; Kubesova, Holik et al. 2006). Thus, providing sufficient education and assistance to better ensure patient compliance with treatment regimens is an important and growing concern among caregivers and insurers.

The general problem of patient compliance has been studied extensively (see, e.g., Herrmann and Gaus 1981; Peck and King 1982; Jay, Lift et al. 1984; Shope 1988; Tollefson 1993; Tamblyn 1996; Collingsworth, Gould et al. 1997; Vrijens and Goetghebeur 1997; Hausman 2001; Garcia Popa-Lisseanu, Greisinger et al. 2005; Mishra, Hansen et al. 2006), as well as in specific diseases including acne (Zaghloul, Cunliffe et al. 2005), osteoporosis (Gold and Silverman 2006), psoriasis (Zaghloul and Goodfield 2004), and cancer (Waterhouse, Calzone et al. 1993). Much has been written about compliance for chronic, long term diseases such as HIV-AIDS (Colombo 1997; Williams 1997; Garcia, Schooley et al. 2003; Goode, McMaugh et al. 2003; Berg, Demas et al. 2004; Carballo 2004; Halkitis, Kutnick et al. 2005; Nischal, Khopkar et al. 2005; Erlen and Sereika 2006; Slama, Le Camus et al. 2006), hepatitis C (HCV) (Braitstein, Justice et al. 2006), diabetes (Schafer, Glasgow et al. 1983; Sung, Nichol et al. 1998; Kalsekar, Madhavan et al. 2006), and treatments for mental illness (Diaz, Neuse et al. 2004; Farabee and Shen 2004; Nakonezny and Byerly 2006).

For example, a patient who is under therapy for a cancer typically takes a combination of prescription and non-prescription medications to help treat the disease and to strengthen his or her overall state of health. Often the patient obtains non-prescription medications, such as various vitamins and other nutraceuticals, from a retailer (either brick-and-mortar or online) in a variety of different forms and pill sizes. He or she further obtains drugs directly from their physician(s) or fills prescriptions with a pharmacist, and then adds the filled prescriptions to their growing collection of drugs. Moreover, the patient can be taking other medications, such as antibiotics, antihypertensives, anxiolytics, and the like to treat other conditions in addition their cancer. Each medication can have a different dosing schedule and can further have complex interactions with other medications, which the patient must keep track of.

One attempt at providing tools for the self-management of medications to patients is illustrated in FIGS. 1a and 1b. The prior art "pill box" provides a plurality of compartments, into which the patient loads the appropriate pill(s). Many different pill box configurations are possible, with individual compartments provided to support various use regimens. "Pill boxes" suffer from requiring the user to track whether they have enough medication to fill a pill box, have properly loaded medicines into the pill box and then whether they took their medication on schedule. Automated "pill boxes" and more complex systems, such as those described in U.S. Pat. No. 6,380,858 to Informedix of Rockville, Md., automate portions of managing a patient's taking their prescriptions, including providing audible reminders and tracking when a pill box provides a pill to a user. Collectively, these prior art medication organizing systems solve some problems while introducing others. Given the importance of this problem, the diversity of treatment regimens and sources of non-compliance, and complexities of reinforcing patient compliance, a variety of medication organizing devices have been devised; however, current devices have serious drawbacks, including:

- Do not address prescription fulfillment issues, including out-of-stock and asynchronous fulfillments;
- Do not address complexities inherent with loading and interacting with the medication organizing device;
- Require the patient to be within audible range of a medication organizing device with audible alerts, which is effective only for persons having a sedentary lifestyle or a limited dosing schedule;

Are physician- or pharmacist-centric, and focus on prescription medications;

Fail to integrate prescription refills, non-prescription medications, and alternate dispensing formats;

Fail to limit the wastage, manage the disposal and permit recycling of unused medications;

Are ineffective at simplifying the life of a medication patient having numerous therapies, often with complex dosing, timing, interactions, and other restrictions; and Are single-location devices.

Prescriptions are typically provided by medical professionals when a patient visits the medical professional, and are generally for fixed durations such as 7, 14, or 30 days, and optionally can be refilled for a period of time or number of doses. A patient or their representative provides these prescriptions to one or more pharmacists for dispensing. The pharmacist typically packages the prescribed medication for the required duration and provides these medication(s) to the patient. The asynchronous nature of the prescribing/dispensing process creates timing issues for managing refills. Some patients end up making trips to the pharmacy on a weekly basis (or even more frequently) to refill prescriptions that have run out or have been newly prescribed by one or more medical professionals. Further, pharmacists ideally will verify the prescriptions as being authentic before dispensing certain medications, and interact with insurers and medication managers in order to assure that medications are being properly prescribed, dispensed, and paid for. In some cases, the pharmacist cannot have sufficient stock of a medication; and he or she must order the stock from a central warehouse, from which they are delivered within a few days. This delay forces the patient to return to pick up a prescription instead of having it filled "on-the-spot."

Also, patients today tend to live more active lifestyles than prior generations; and hence they tend to be away from traditional sources of medications, such as their local pharmacy and doctor's office. At the same time, medication regimens are becoming increasingly precise as to when specific doses must be taken, and medication management providers are increasingly restrictive as to how many doses can be dispensed to a patient. Thus, patients suffer from forgetting to take a timed dosage, losing doses, not having specific doses available when needed, having to manage refills of numerous medications as they run out at inconvenient times, and other issues that inhibit the patient's taking of the necessary doses at the proper time. All of these factors together increase the risk of non-compliance with medication regimens.

4 SUMMARY OF THE INVENTION

The invention consists of a Medication Management System ("MMS") comprising various systems that serve various stakeholders, hardware devices, computer software systems, standards, methods, procedures, practices and their interconnection in ways that lead to greater efficiency, safety, and efficacy, along with potentially lower cost and less wastage in the delivery of, and monitoring patient compliance with use of, medications, whether prescription or not.

In one aspect, the present invention provides a method for determining whether a package has been opened. In one embodiment, the method of the invention comprises: providing a package including at least first and second radiofrequency identification (RFID) tags that are arranged in the package such that opening the package renders the first RFID tag inoperative while leaving the second RFID tag operative. The method includes monitoring the status of the two RFID tags. If the first RFID tag is detected to be inoperative, then the package is determined to have been opened.

In some embodiments, the method further includes configuring the first RFID tag to have at least two portions, wherein one portion is a perforated portion; and arranging the first RFID tag in the package such that opening the package is effective to separate the first RFID tag into the at least two portions thereby rendering the first RFID tag inoperative. In other embodiments including these features, one of the two portions is the antenna of the first RFID tag.

In a second aspect, the present invention provides a package comprising a first RFID tag and a second RFID tag, the first and second RFID tags arranged such that opening the package renders the first RFID tag inoperative. Other embodiments include those described above wherein the second RFID tag is arranged in the package such that the second RFID remains in the package after the package in opened. Yet other embodiments include those described and further comprising storing an indicator of the relationship between the package and the first and second RFID tags in a database.

In a third aspect, the present invention provides a system for monitoring the status of a package. In some embodiments, the system comprises a package including a first RFID tag and a second RFID tag, the first and second RFID tags being arranged such that opening the package renders the first RFID tag inoperative; a database that includes entries for the statuses of the first and the second RFID tags; and an RFID monitor that detects whether each of the first and the second RFID tags are operative. Other embodiments further include an entry for the status of the package, wherein the status of the package is dependent at least in part on the statuses of the first and the second RFID tags. Still other embodiment include those wherein the second RFID tag is configured to store information about the contents of the package.

In a fourth aspect, the present invention provides a dual RFID tag, comprising a first RFID tag and a second RFID tag, the first RFID tag being configured so that the first RFID tag can be rendered inoperative while the second RFID tag remains operative.

These and other aspects and advantages will become apparent when the Description below is read in conjunction with the accompanying Drawings.

5 BRIEF DESCRIPTION OF THE DRAWINGS

Figure 1B:
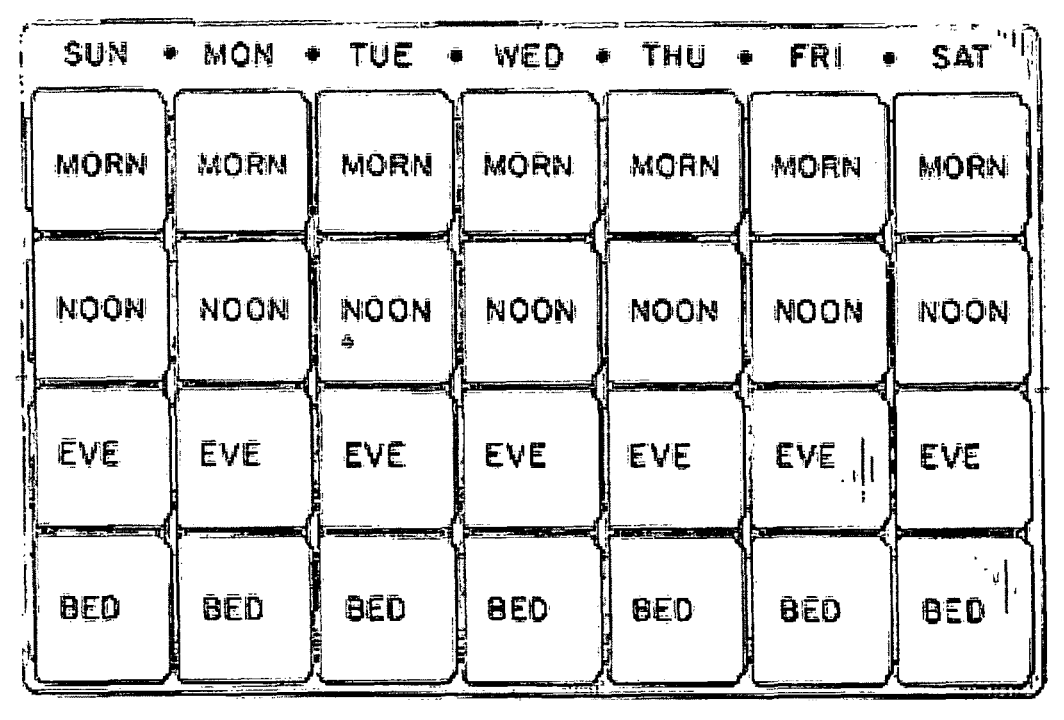

FIGS. 1a and 1b illustrate examples of medication organizing and dispensing devices in the prior art.

FIGS. 2a through 2c illustrate a Medication Management System ("MMS") in accordance with the present invention. FIG. 2a depicts some possible Stakeholders, and two main features facilitating interaction, of an embodiment of MMS in accordance with one embodiment of the invention. FIG. 2b depicts an embodiment of some MMS Devices and their arrangement in the MMS architecture in accordance with one embodiment of the invention. FIG. 2c depicts a possible embodiment of an MMS Database architecture.

FIG. 5a depicts an example Medication Dispensing Device (MDD) of the present invention.

FIG. 5b depicts the components of an example medication handler subsystem of an MDD of the present invention. FIG.

5c depicts the components of an example medication dispenser subsystem of an MDD of the present invention.

Figure 6:
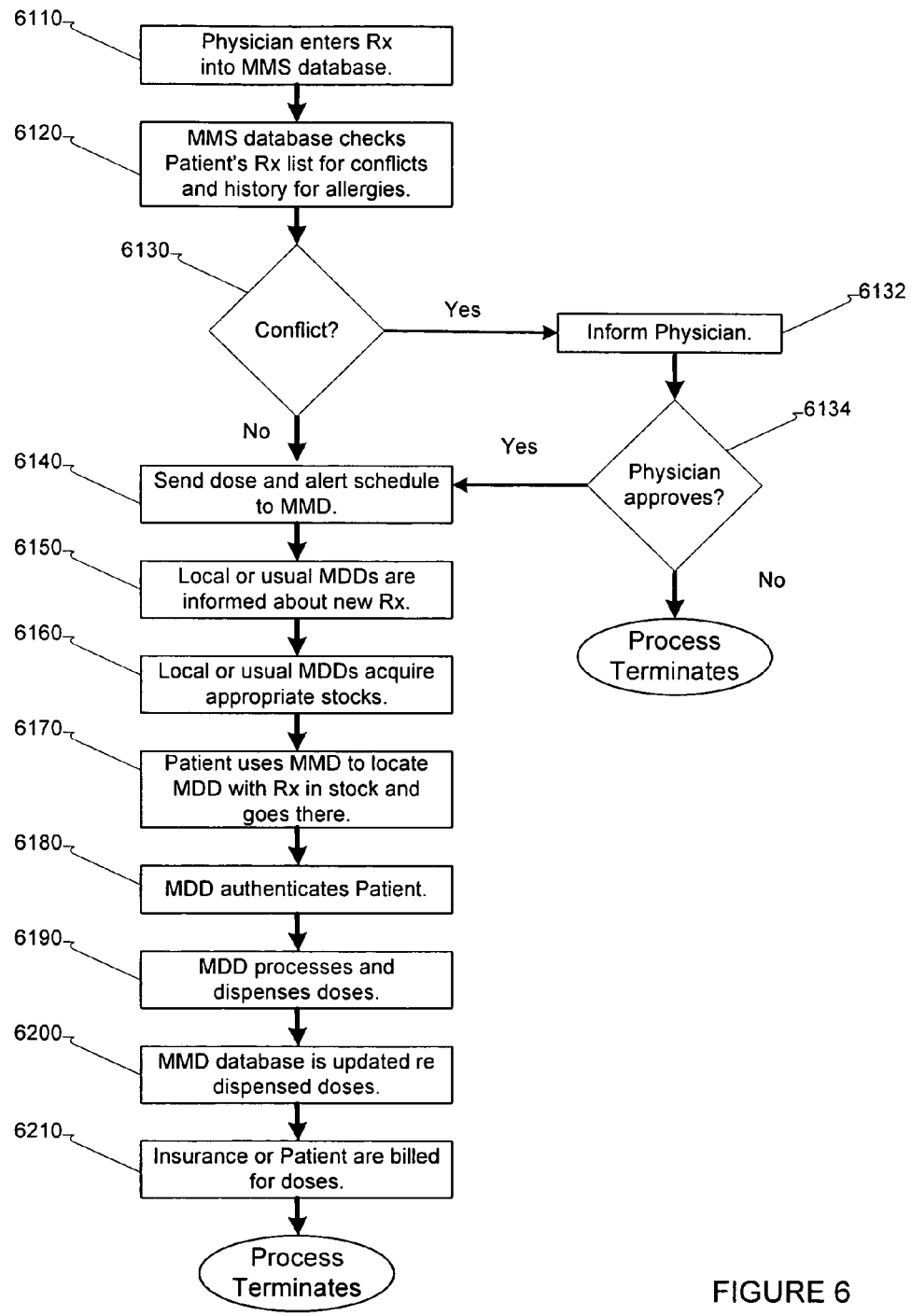

FIG. 6 is a flowchart depicting the steps in a possible Procedure for a patient receiving medications from an MMS.

Figure 7:
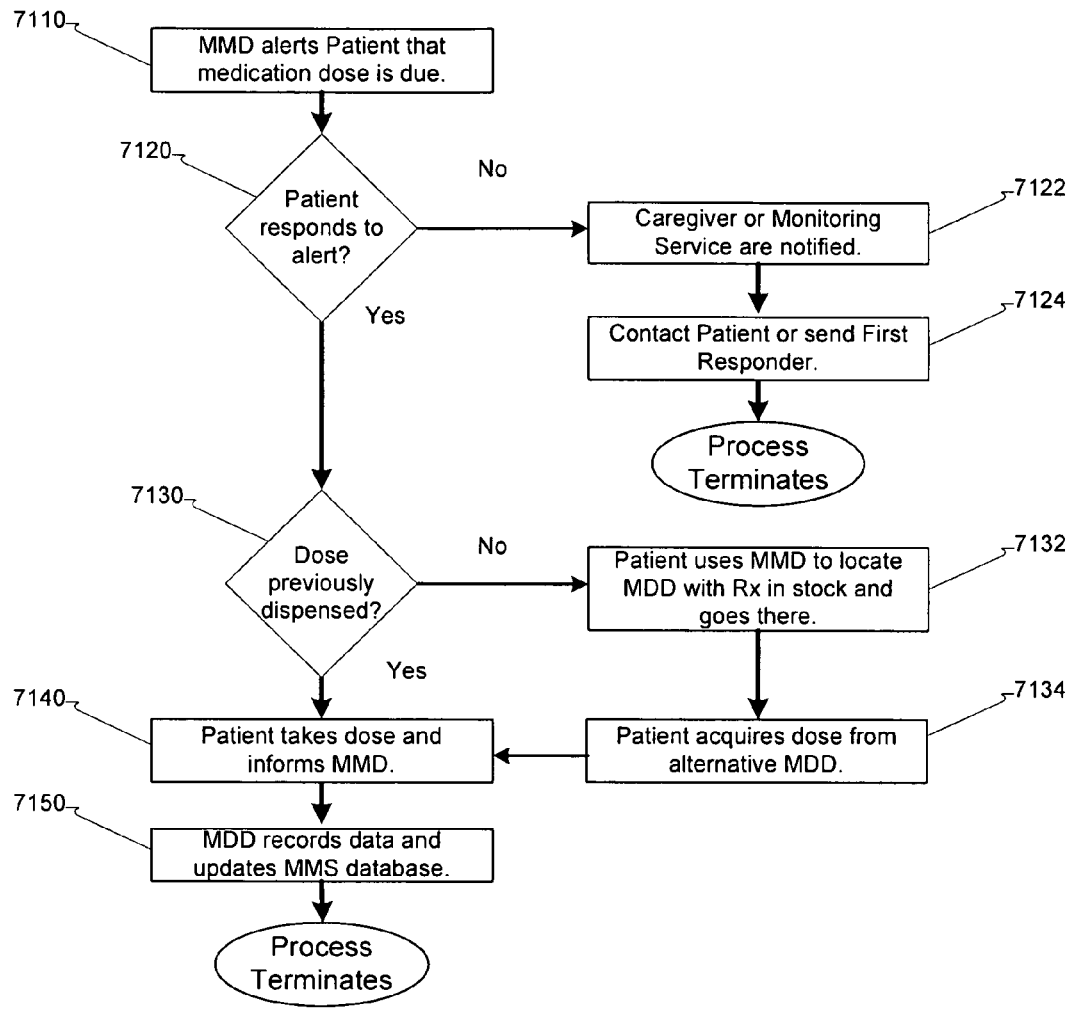

FIG. 7 is a flowchart depicting the steps in a possible Procedure for a patient to take a scheduled dose of medication using features of an MMS.

Figure 8:
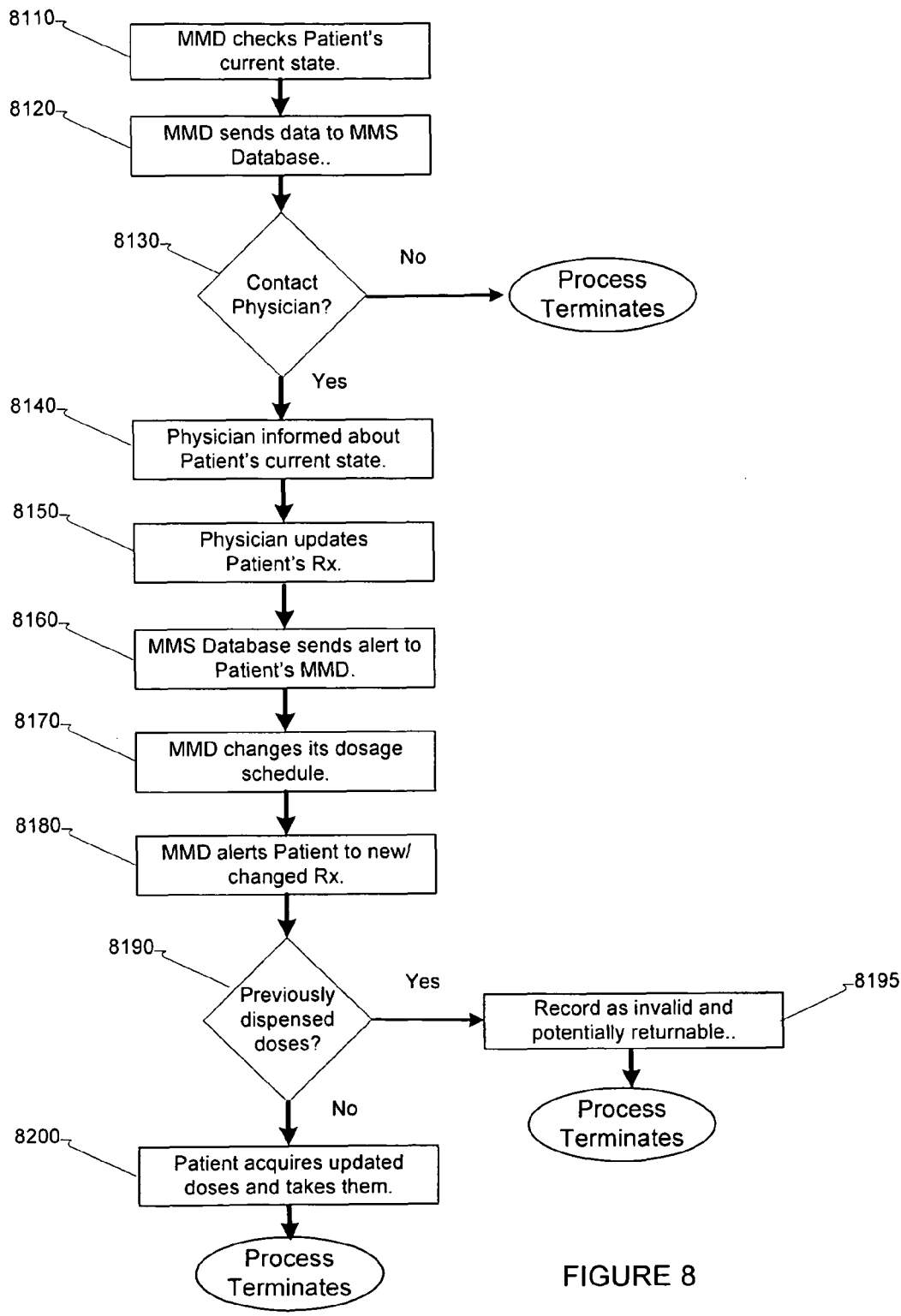

FIG. 8 is a flowchart depicting the steps in a possible Procedure for changing a patient's prescription within an MMS.

Figure 9:
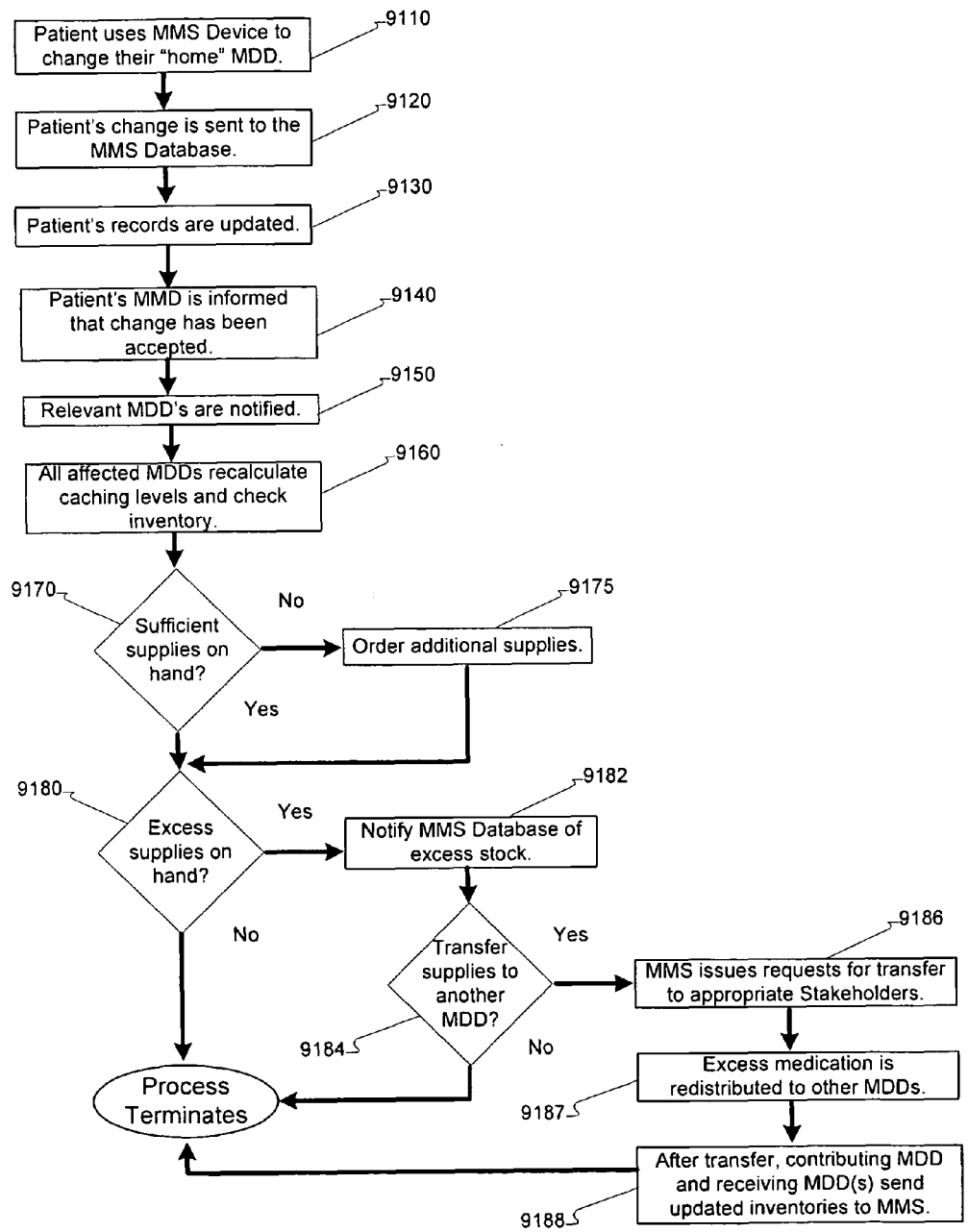

FIG. 9 is a flowchart depicting the steps in a possible Procedure for changing a patient's designated "home" Dispensing Provider from one device to another.

Figure 10:
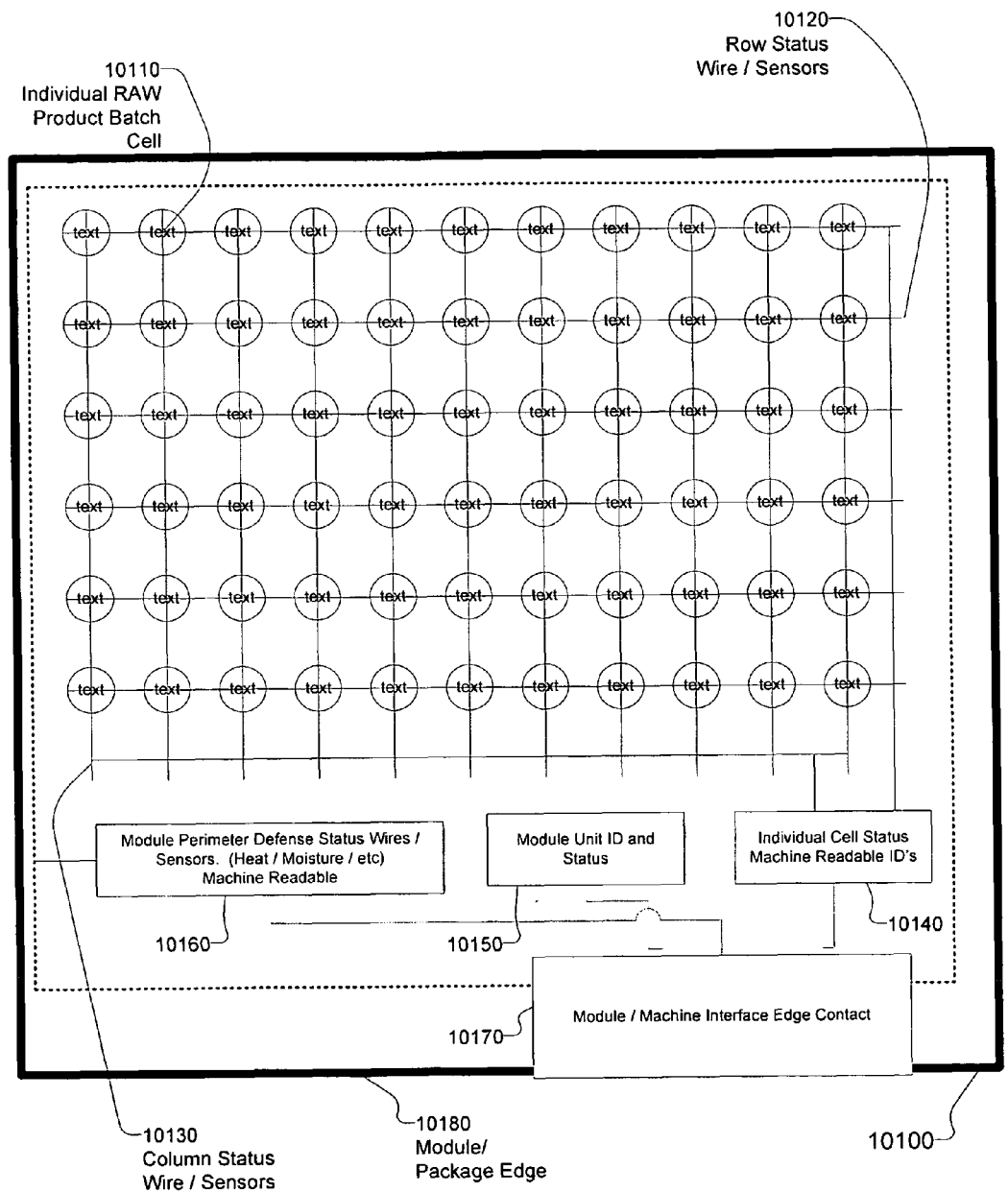

FIG. 10 depicts a loading module for the MDD, where each cell is of the same content size.

Figure 11:
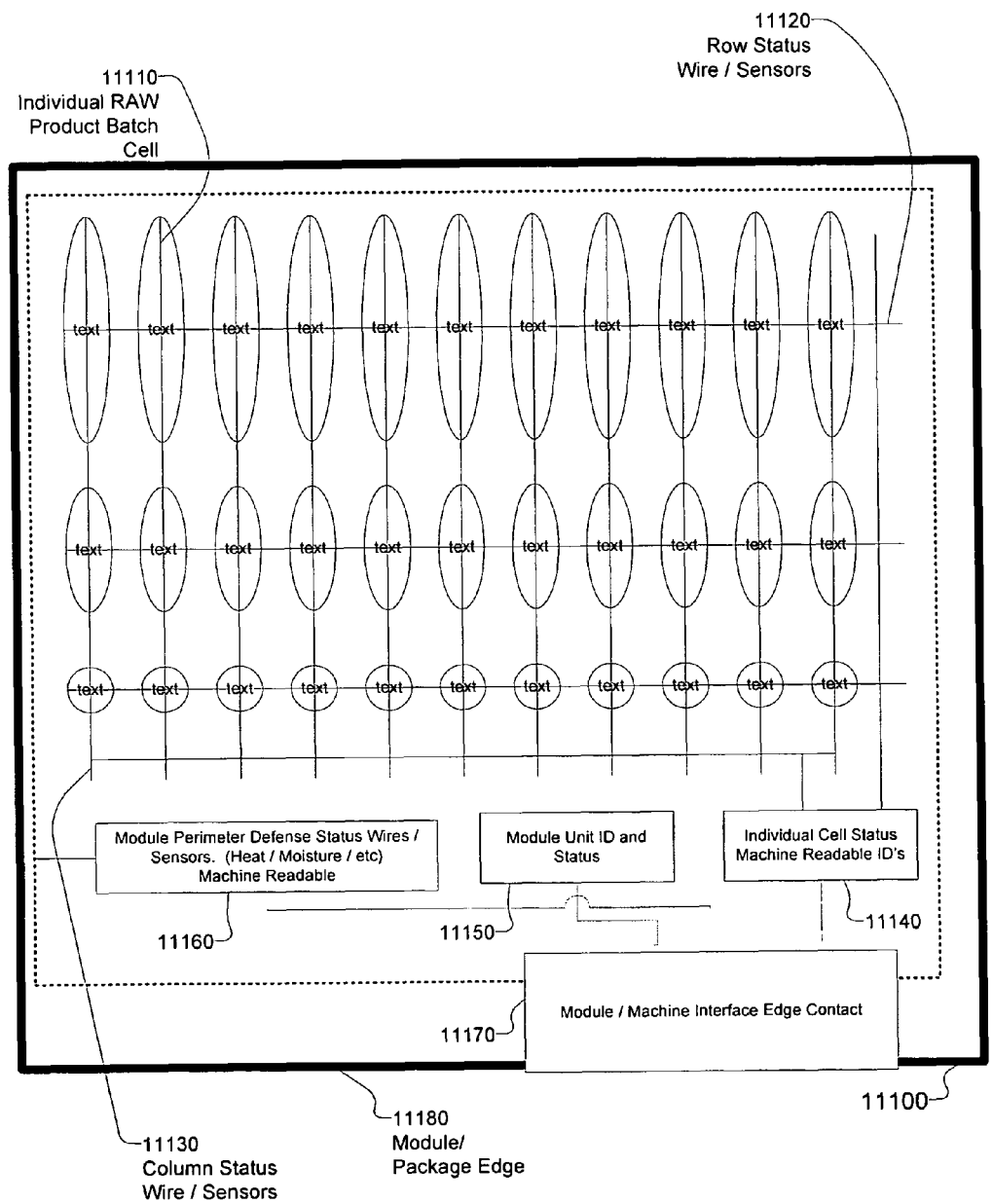

FIG. 11 depicts a loading module for the MDD, where the cells are of varying content size.

Figure 12A:
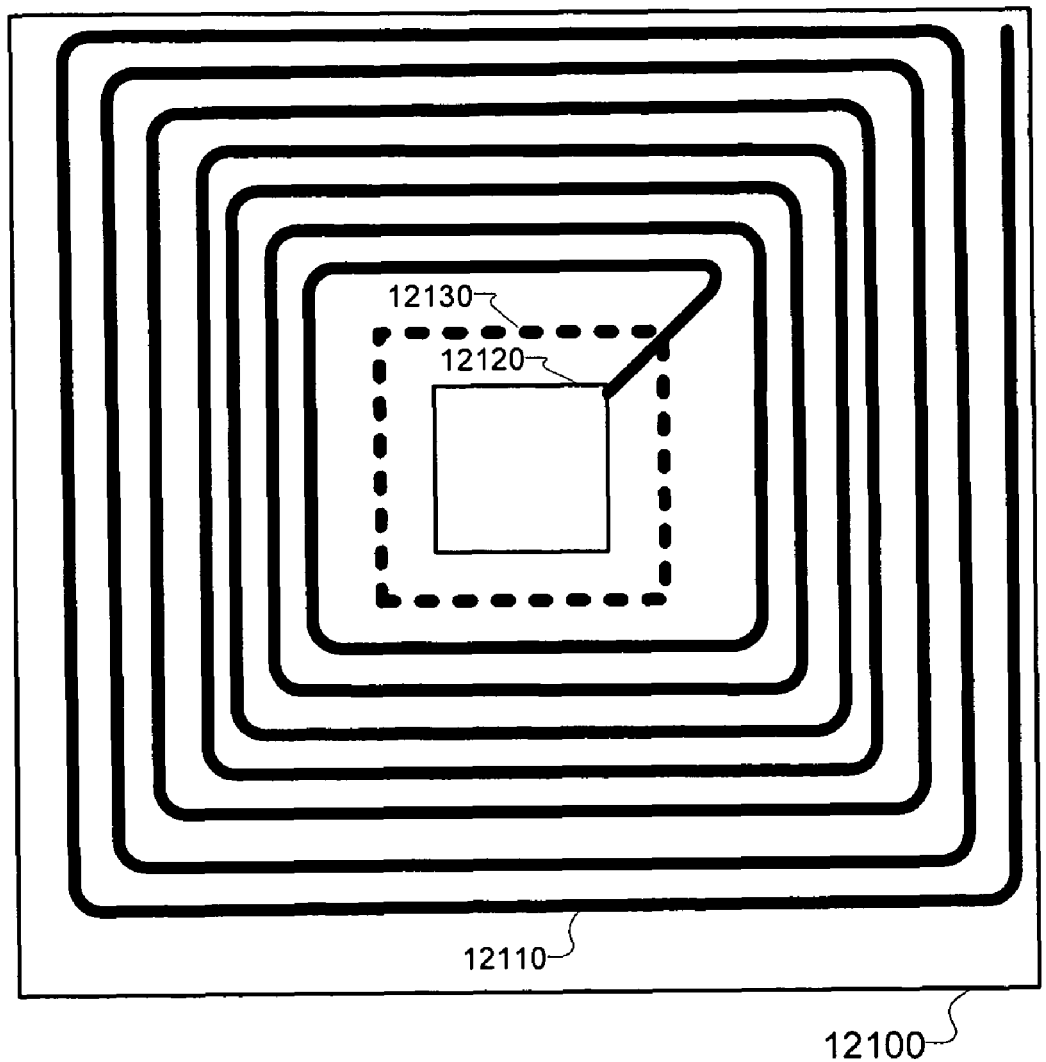
Figure 12B:
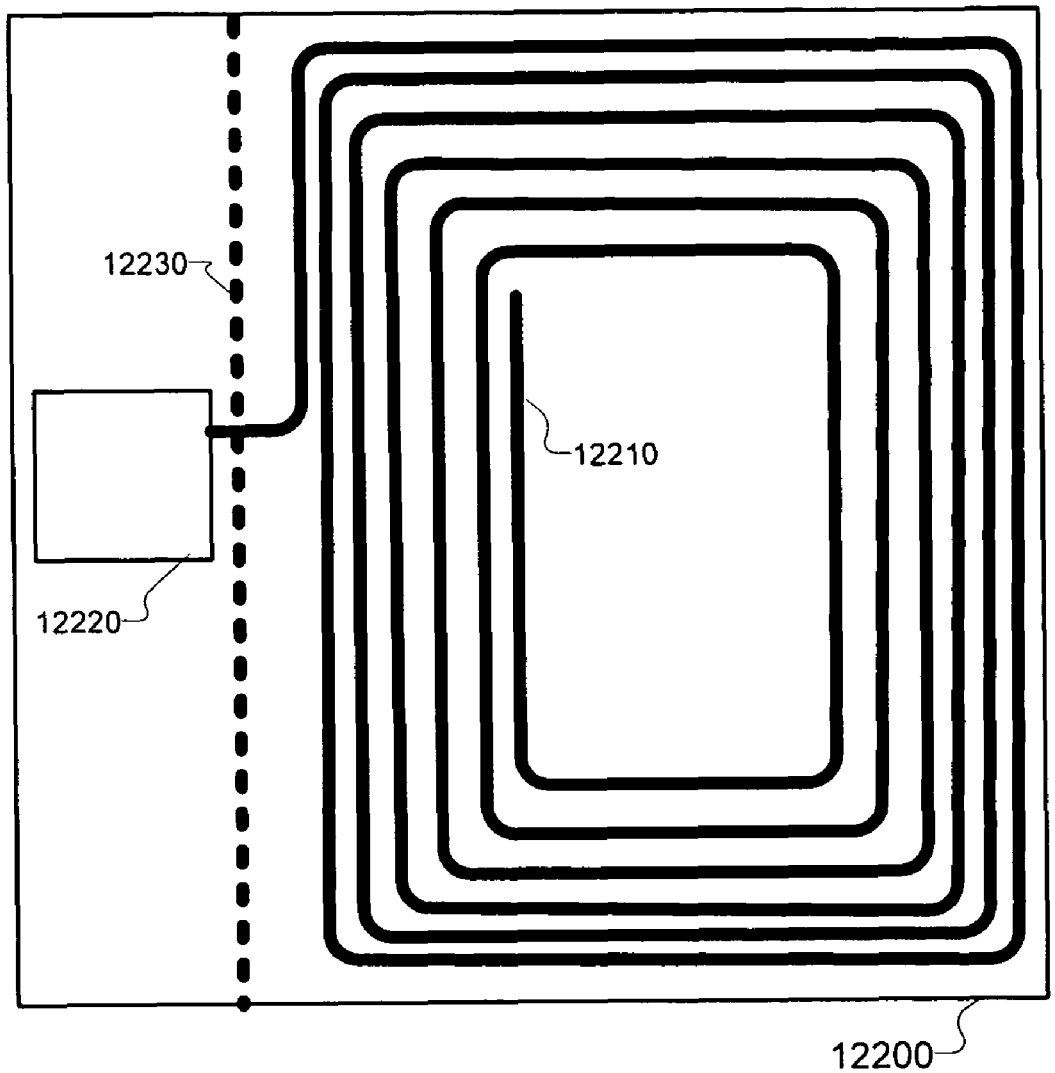

FIGS. 12a and 12b depict exemplary RFID tags with perforations to render the tag unusable when a package is opened.

Figure 13:
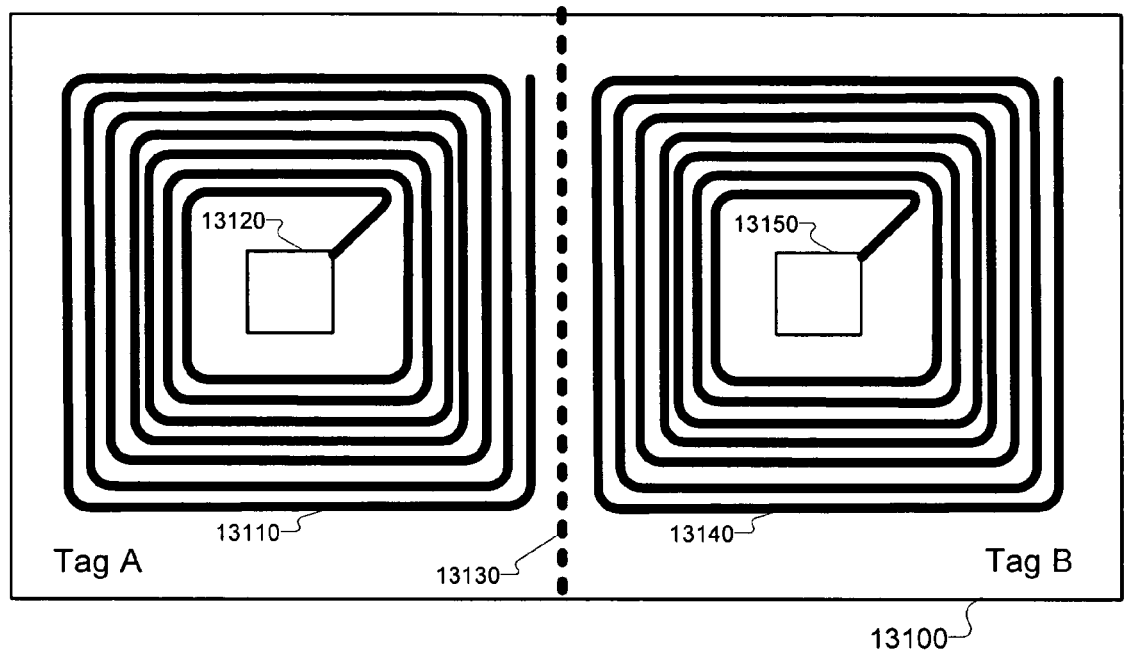

FIG. 13 depicts an exemplary set of "paired" RFID tags with perforations to remove one of the tags when a package is opened.

Figure 14:
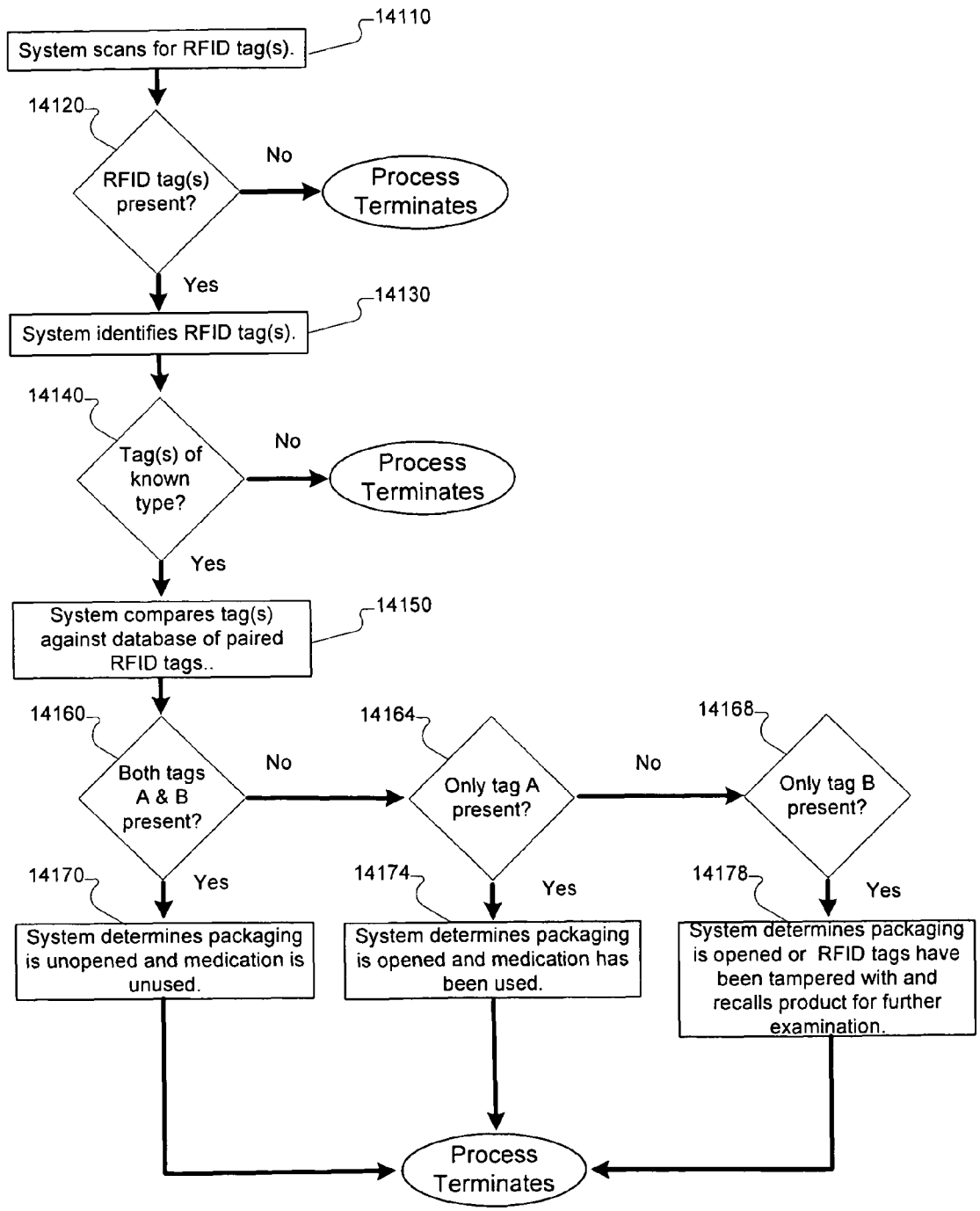

FIG. 14 is a flowchart depicting the steps in a possible Procedure for determining the state of a package using a set of "paired" RFID tags.

6 DESCRIPTION OF SOME EMBODIMENTS OF THE INVENTION

6.1 Definitions

The following definitions are used throughout, unless specifically indicated otherwise:

| Term | Definition |
| --- | --- |
| Medication Organizing Device | Any prior art device for organizing medications, ranging from pill boxes to pill delivery machines. These devices typically dispense pre-packaged or pre-produced medications (such as pills). |
| MDD | Medication Dispensing Device. This an MMS-enabled device for dispensing medications, preferably at a Dispensing Provider. |
| MMD | Medication Management Device. A communications interface that communicates alerts to a patient, sends patient compliance data to the rest of the MMS and/or performs other functions as deemed useful. The MMD can be incorporated at the facility of a Dispensing Provider or can be a separate device or consist entirely of software running on other devices not specific to the MMS. It can also have interfaces for devices such as patient data sensing equipment. |
| MMS | Medication Management System. This is the combination of hardware and software, along with any related procedures, methods and practices, which make up the invention. |
| MMS Communications and Networking system | The collection of hardware, software, and data systems used by an embodiment of the invention for internal communication between elements of the MMS. |
| MMS Database | The virtual database comprised of all data required for the proper functioning of the MMS, however stored, accessed, or maintained in an actual embodiment of the invention. |
| MMS Device | A device, such as an MMD, which is designed for, or used as part of, an MMS. |
| Package | Any type of container, such as an envelope, pouch, bottle, blister pack, box, or the like, that can be sealed in such a way that opening the package breaks its integrity with respect to the contents held in the package. Although the invention is exemplified using embodiments that include package containing medicaments, it will be understood herein that the invention is not so limited, and that the term package can be for any purpose and contain any material. |
| RFID tag | A device having an antenna to receive and transmit information by radio, in addition to some capability for local data storage and processing, that can recognize the radio signal, and respond to the received signal by transmitting data. The device can also include power, such as from a local power source (battery). The device may also include one or more probes that can sense (and optionally store) ambient conditions (e.g., temperature). |
| Stakeholder | Those entities involved with the functioning of some aspect of the MMS. |

6.2 Medication Management System Architecture

Figure 1A:
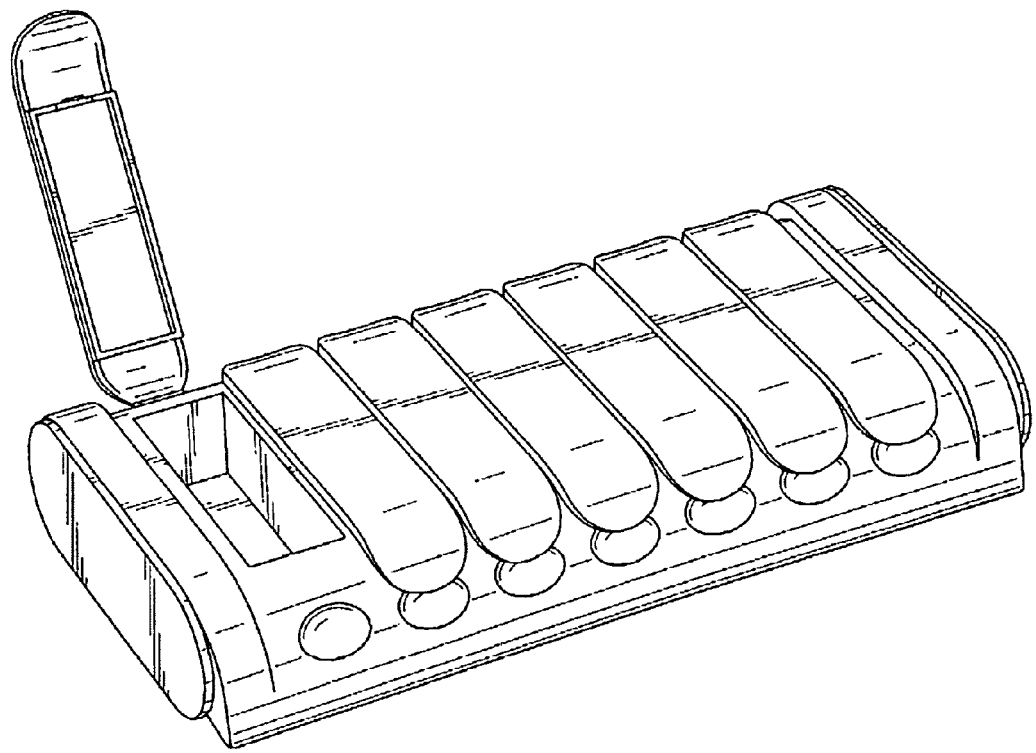
Figure 2A:
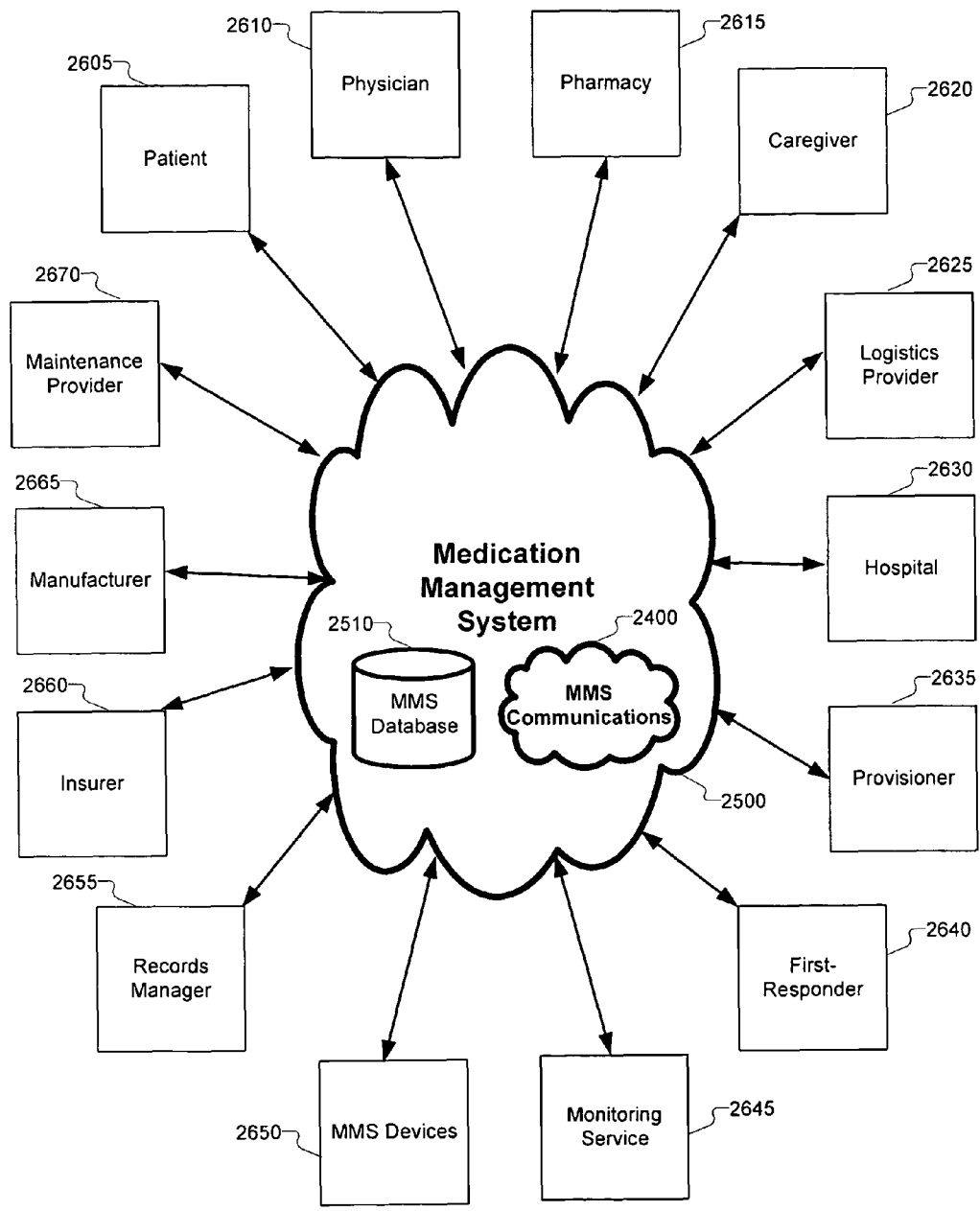
Figure 2B:
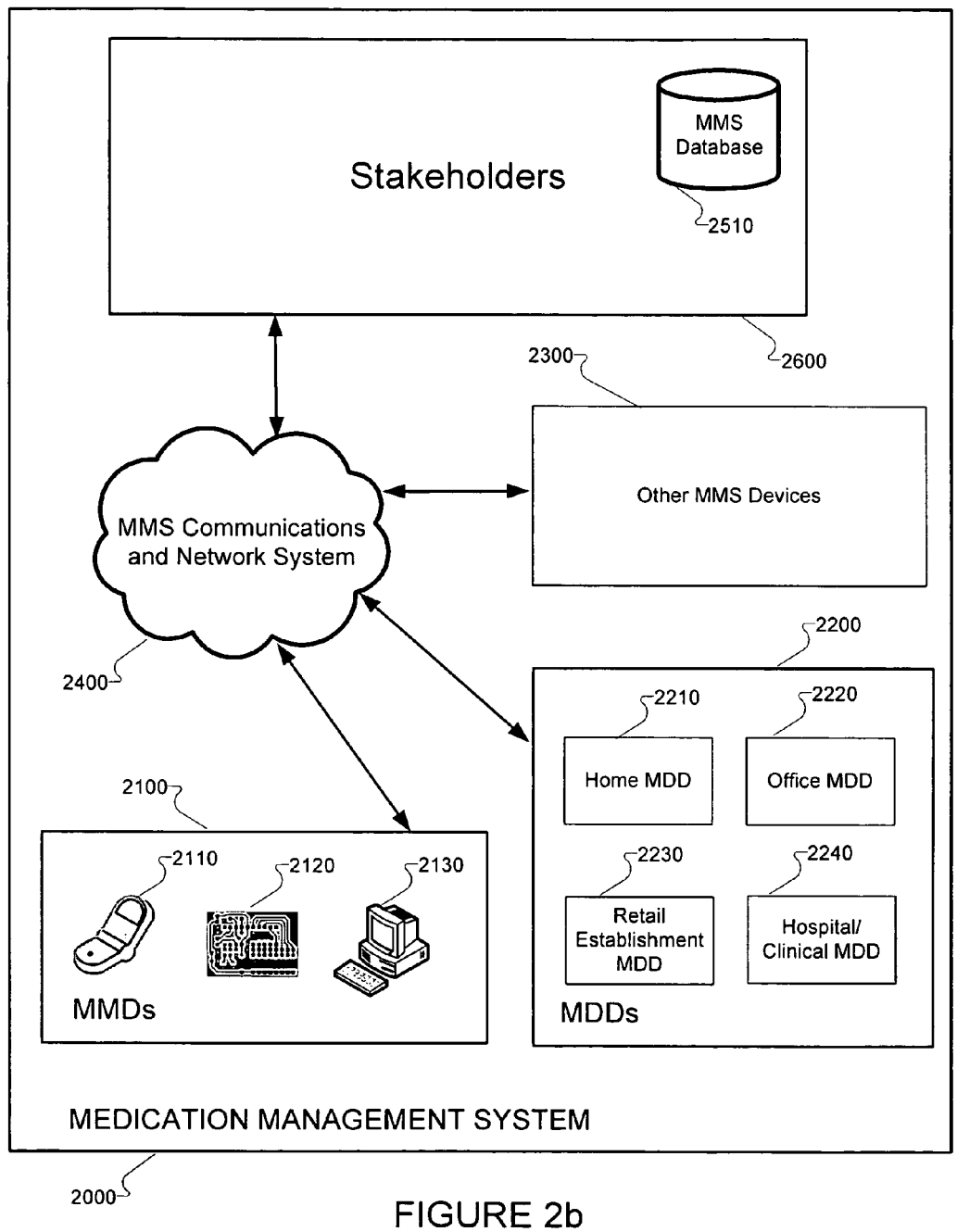

FIG. 2a depicts an embodiment of a Medication Management System ("MMS", 2500) provided by the present invention. The MMS (2500) coordinates the activities of various entities, called Stakeholders (2605-2670), who share responsibility for enabling, monitoring, and enforcing patient compliance by facilitating the integration of their activities within the Medication Management System of the invention and allowing synergies not otherwise possible or economical. In a more specific embodiment, the MMS (2500) integrates the existing needs and capabilities of each Stakeholder (2605-2670) to provide effective management of medications to patients. In a still more specific embodiment, as depicted in FIG. 2b, the MMS (2000) incorporates one or more MMS Devices, such as Medication Management Devices (2100) ("MMDs") (2110, 2120 or 2130, individually or in combination) which can be widely deployed in a variety of configurations and capabilities and interconnected using common technologies with the computer and business systems of the Stakeholders (2600), or with other MMS Devices (2300), through the MMS Communications and Networking system (2400). Information necessary for the proper functioning of the MMS is stored in the MMS Database (2510), which can be centralized, replicated, dispersed, or kept in any other manner and form that is determined to be proper and adequate by those having skill in the art.

Returning to FIG. 2a, the Stakeholders (2605-2670) whose activities are integrated by the MMS, some of which are depicted in the Figure, include without limitation: patients (2605), Physicians (2610), Pharmacists (2615). Caregivers (2620), Logistics Providers (2625), Hospitals (2630), Provisioners (2635), First Responders (2640), Monitoring Services (2645), MMS Devices (2650), Records Managers (2655), Insurers (2660), Manufacturers (2665), and Maintenance Providers (2670). Other possible Stakeholders within the scope of the present invention include, without limitation: clinical and hospital laboratories, doctor's offices, retail establishments, offices; and commercial settings where availability of medication management and medication dispensing services are desirable, such as hotels and cruise ships. In some cases, several Stakeholder roles can be combined within the operations of one particular company or entity. In other cases, various aspects of a single Stakeholder role can be divided between multiple companies or entities. An MMS also integrates a plurality of MMS Devices (MMDs, and/or other required devices) with the information systems of MMS Stakeholders through aspects of the MMS Database and the MMS Communications and Networking System.

In one embodiment, an MMS facilitates patient care through the use of "electronic medication records." In traditional models, a prescription for a specific medication indicates the dosage, the number of doses per day, and a specific medication. A pharmacist generally dispenses the entire amount of the prescribed medication in a single transaction. This contributes to the waste of the medications if a patient is unable to complete a medication due to side effects or other reasons. An MMS, through its MMDs. interacts directly with an electronic prescription to record dispensed medications in accordance with an electronic prescription. An MMS, through its MMDs. interacts directly with an electronic medication record to record dispensed medications in accordance with an electronic medication record. Furthermore, in some embodiments of the invention, an MMS, through its Dispensing Providers, can track and manage custom dosages of medications on an individualized basis and track the customized dosage instead of a standardized dosage. This allows medication to be tailored more precisely to the needs of the patient, even on a dose-by-dose basis, with adjustments made as required. One aspect of the use of an MMS-aware Dispensing Provider is that electronic medication records can be partitioned into individual doses, and can be managed at the individual dose level instead of at the level of the entire prescription, thus achieving lower wastage, better effectiveness, and reduced chance of adverse side-effects. This can be accomplished using a variety of approaches. In a first approach, a connected interaction between Stakeholders can be used. An alternate approach uses a variant of Chaumian digital cash and provides for bearer electronic prescriptions that can be partitioned as individual doses without requiring a real time connection.

6.2.1 Stakeholder Roles

In an MMS, Stakeholders take on various roles required by the system. A Stakeholder can fill one role in the system (e.g. patient), perform multiple roles (e.g. an Insurer can perform Records Management as well as be a Monitoring Service, or a Maintenance Provider can also function as a Provisioner) or share a role with another Stakeholder (e.g. two Physicians can consult on a patient's care, or a patient can have more than one Insurer). Different Stakeholders can perform the same role (e.g. a Pharmacy, Physician, Provisioner (collectively, a "Dispensing Provider") or patient can each provide materials managed by an MMS). Stakeholders are those involved with the functioning of some aspect of the MMS, and roles are collections of actions and responsibilities that must be carried out to cause the MMS to function. The mapping between these is not limited or fixed over time. The only requirement is that all roles necessary to the functioning of a particular implementation of an MMS be carried out.

The roles in an MMS can include, but are not limited to, the following.

| Role | Description | Interactions with other Roles |
|---|---|---|
| patient | A person needing medicine and/or monitoring. | Pharmacy - Convey Prescription, Insurance Information, Query/Response, Authentication, Compliance Data. Physician - Convey patient Medical History, Current patient Condition, Insurance Information, Alert Message, Query/Response, Authentication, and/or Compliance Data. Caregiver - Convey patient Medical History, Current patient Condition, Insurance Information, Alert Message, Query/Response, Authentication, and/or Compliance Data. Hospital - Insurance Information, Query/Response, and/or Authentication. Insurer - Insurance Information, Alert Message, Query/Response, and/or Authentication. Maintenance Provider - Insurance Information, Service Request, Alert Message, Query/Response, and/or Authentication. Monitoring Service - Current patient Condition, Insurance Information, Service Request, and/or Authentication. Records Manager - Query/Response, and/or Authentication. First Responder - Prescription, patient Medical History Current patient condition, Query/Response, Authentication, and/or Compliance Data. |
| Pharmacy | A retail supplier of medical substances, including prescription medications. | Insurer - Insurance Information, Query/Response, Authorization, and/or Stocking Information. Provisioner - Receive Service Request, Authentication, Authorization, send prepared Dispensing Provider supply materials though Logistics Provider. Logistics Provider - Ship prepared Dispensing Provider supply materials. Records Manager - Update Stocking Information, and/or Query/Response. |
| Physician | A doctor permitted to prescribe medications for a patient. | patient/MMD - Get patient Medical History, Current patient Condition, Insurance Information, Alert Message, Query/Response, Authentication, and/or |

-continued

| Role | Description | Interactions with other Roles |
|---|---|---|
| | | Compliance Data. Pharmacy - Send Prescription, Authentication, and/or Authorization. Caregiver - Query/Response, Compliance Data, Authentication and/or Authorization. Insurer - Request payment, Authentication, and/or Authorization. Monitoring Service - Alert Message, Query/Response, Current patient Condition, and/or Authentication. Records Manager - Update patient Medical History, Query/Response, and/or Authentication. |
| Caregiver | Any nurse, physical therapist, or other person who provides care but is not permitted to prescribe medication. | patient - Current patient Condition, Insurance Information, and/or Compliance Data. Physician - Alert Message, Current patient Condition, Query/Response, Authentication, and/or Authorization. Insurer - Arrange Payment. |
| Hospital | Any hospital, clinic, or other provider of care services where physicians and caregivers work. | patient - Get Insurance Information, Query/Response, and/or Authentication Insurer - Arrange Payment, and/or Authorization. |
| Insurer | Insurance companies, or their medical management companies or any other entity involved in paying for, authorizing payment for, or limiting selection of treatment or medications for a patient. | patient - Alert Message, Query/Response, Insurance Information, Authentication, Authorization, and/or Arrange Payment. Pharmacy - Arrange Payment, Authentication, and/or Authorization. Physician - Arrange Payment, Authentication, and/or Authorization. Caregiver - Arrange Payment, Authentication, and/or Authorization. Hospital - Arrange Payment, Authentication, and/or Authorization. Maintenance Provider - Arrange Payment, Authentication, and/or Authorization. Provisioner - Arrange Payment, Authentication, and/or Authorization. Monitoring Service - Arrange Payment, Authentication, and/or Authorization. Records Manager - Arrange Payment, Authentication, and/or Authorization. Manufacturer - Arrange Payment, Authentication, and/or Authorization. First Responder - Arrange Payment, Authentication, and/or Authorization. |
| Maintenance Provider | A person or company that deals with maintenance, repair, or re-provisioning of MMS Devices. | patient - Query/Response to arrange scheduling and/or Authentication. Insurer - Arrange Payment, Authentication and/or Authorization. Monitoring Service - Service Request, Query/Response, and/or Authentication. Manufacturer - Service Request, Query/Response, Authentication and/or Authorization. |
| Provisioner | A person involved in re-provisioning of MMS Devices. | patient - Query/Response to arrange scheduling and/or Authentication. Pharmacy - Service Request, and/or Authentication. Insurer - Arrange Payment, Authentication, and/or Authorization. Logistics Provider - Receive supplies. Monitoring Service - Service Request, and/or Authentication. Records Manager - Stocking Information and/or Authentication. |
| Logistics Provider | A person or company involved in the transport of items from one place to another. | Pharmacy - Receive supplies for Provisioner. Maintenance Provider - Deliver parts and supplies from Manufacturer. Provisioner - Deliver supplies from Pharmacy. Manufacturer - Receive parts and supplies for Maintenance Provider. |
| Monitoring Service | A person or company that provides monitoring services. These can be patient | patient - Receive Current patient Condition, and/or send/receive |

| Role | Description | Interactions with other Roles |
|---|---|---|
| | monitoring, security monitoring, data monitoring, records auditing, or any other kind of monitoring activity for the MMS. | Query/Response.<br>Physician - Send Alert Message, send/receive Query/Response, and/or Authentication.<br>Caregiver - Send Alert Message, send/receive Query/Response, and/or Authentication.<br>Insurer - Arrange Payment, Authorization, and/or Authentication.<br>Maintenance Provider - Send Service Request, Query/Response, and/or Authentication.<br>First Responder - Send Alert Message, Query/Response and/or Authentication. |
| Records Manager | A person or company that provides records storage, retrieval, and access control for MMS information. | patient - Query/Response, Authentication and/or patient Medical History.<br>Physician - Receive updated patient Medical History. Query/Response, and/or Authentication.<br>Caregiver - updated patient Medical History. Query/Response, and/or Authentication.<br>Insurer - Query/Response, patient Medical History, and/or Arrange Payment. |
| Manufacturer | A person or company that produces consumables for MMS Devices, or which produces the MMS Devices themselves. | Insurer - Arrange Payment Query/Response, Authentication and/or Authorization.<br>Maintenance Provider - Service Request, Payment Request, Authentication and/or Authorization.<br>Provisioner - Service Request, Payment Request, Authentication and/or Authorization.<br>Logistics Provider - Send parts and supplies for Provisioners and/or Maintenance Providers. |

Stakeholders can use the capabilities of an MMS in various ways that exploit the advantages provided by the MMS. In a first example embodiment, the tracking of prescriptions and other medications using an electronic medication record instead of physical prescriptions reduces errors in prescribing and reduces prescription fraud. Secondly, the largely nonstandard area of over-the-counter medications and nutraseuticals can be integrated into the management regime, by creating electronic medication records within an MMS of over-the-counter medications and nutraseuticals as they are purchased and subsequently consumed. Standard dosage, composition, and other information about the over-the-counter and nutraseuticals purchased can be automatically integrated as electronic medication records with one or more MMS at point of purchase, at the consumers home, or at other locations. The conversion of purchased items to electronic medication records can occur automatically from MMS-enabled cash registers at a retailer, by scanning the barcode on the over-the-counter medication or nutraseutical container (either at the retailer or at the consumers home or other location using an MMS-enabled device), or by entering the barcode or other identifying information into an MMS-enabled device or kiosk. Integrating the management of over-the-counter medicines and nutraseuticals in this way permits one or more MMS Stakeholders to have a more accurate view of the medications and nutraseuticals being taken by a patient. An immediate benefit is the ability of MMS stakeholders to detect medication interactions. Extending this benefit to include a patient's non-prescribed medications extends the view of medical professionals to include more of the patient's lifestyle, and reduces medication interactions between prescription and non-prescription medications and nutraseuticals.

Patients also benefit by tracking medications of all types using an MMS. First, the patient receives the benefit of better-informed medical care. Secondly, and more important to the patient, is that they:

Have a central record of all their medications; prescription, over-the-counter, and nutraseuticals without being required to understand, maintain, and manage these records.

Have benefit of receiving integrated services from one or more Stakeholders without increasing the patient's workload. Thus, if the patient is running out of a particular nutraseutical, they can have it automatically reordered as the number of doses becomes low.

6.2.2 MMS Devices

An MMS can be configured to incorporate specialty and general purpose computing devices to facilitate the Stakeholder interactions and reporting required. These specialty and general purpose computing devices are called "MMS Devices" (2650, FIG. 2a). MMS Devices can be used by various Stakeholders to assist with communication, medication compliance management, medication storage, medication tracking, medication dispensing, records management, patient monitoring, or any other functions as determined to be appropriate by each MMS Stakeholder. MMS Devices can be implemented as single user, multi-user, public, private, shared simultaneously, shared sequentially, or any combination of these over time. Similarly, MMS Devices can be purpose-built for use as part of an MMS, or they can be general-purpose computing or consumer devices, adapted through software and/or hardware additions, deletions, or modifications. For example, in some embodiments, standard hardware devices such as cellular telephones can be extended with hardware, and/or software, and/or or connectivity to use these common devices as MMS Devices.

In some embodiments, the MMS Devices are configured for different uses and markets. In more specific embodiments, a first MMS Device is designed for the home market (2210, 2110) and a second MMS Device with differing capabilities or form factor (or both) are deployed as a kiosk in a clinic (2240, 2120) or office setting (2220). In other more specific embodiments, MMS Devices can be deployed that provide a Stakeholder interface to one or more MMSs. For example, network-based application technologies such as remote database access, web pages and mobile applications can be made part of an MMS device for use in interfacing with an MMS.

Some MMS Devices can have additional capabilities, such as the ability to interface with patient state sensors, and to use or relay patient state data as authorized by an MMS. Exemplary patient state data can include, without limitation, blood pressure, heart rate, EKG readings, blood sugar analysis, blood oxygenation levels, and/or body temperature. patient state sensors include those capable of collecting patient state data and can include those capable of interfacing directly with MMS Devices so as to transfer patient state data as well as those which transfer their data using an appropriate medium, such as magnetic recording media, removable flash memory media, or other transfer means. patient state data may be used by Stakeholders, such as Physicians or Caregivers, to track patient response to medication, adjust dosage levels, or make other decisions about patient needs and proper treatment regimens, thus reducing the chances of over- or under-medication, adverse reactions, or undetected condition changes. An MMS can interface with other types of MMS Devices (2300), or MMS devices with alternative capabilities, in addition to, or instead of the exemplary MMDs and/or Dispensing Providers described herein.

In other embodiments, an MMS has the ability to associate multiple MMS Devices with one or more patients.

In some instances this is a convenience feature, allowing, for example, the use of a home (2210) and an office (2220) Dispensing Provider, or a home MMD (2130) and a portable MMD (2110), or a doctor's office MMD or other arrangement as appropriate. In other instances, this can be required due to the limitations of some MMS Devices. For example, a software-based MMD embodiment operating on an industry standard wireless device, such as a cell phone, can be adequate for patient alerts and communication of compliance data, but not have the interfaces required to collect and transmit patient monitoring data from patient sensor equipment, such as heart monitors, which a different embodiment of an MMD might be capable of. An MMS can also specify a "guest" MMD, kiosk, or Dispensing Provider function, to allow a patient to use MMS Devices other than those normally associated with the patient when this is required or desirable. Such flexibility in device availability reduces the chance that a patient will be unable to access required medication at the required times, or will fail to be alerted when a dose is due, even if the patient is moving from location to location throughout the treatment period.

In still other embodiments, the MMS Device is categorized as "public" or "private," based upon the number and/or relationships of its expected user or users. An example of a private MMS Device is one within a specific end-consumer's home that is optionally shared by a small number of related patients. MMS Devices need not solely be used within a patient's home or residence, but can be made available as part of a broader medication management system. MMS Devices can be made available in places such as retail stores, hotels, cruise ships, hospitals and clinics, and in other places frequented by the public. This increases the convenience to the patient by making their medications available in various locations that they are likely to frequent. These "public" MMS Devices provide unique capabilities to an MMS. For example, an office building can have a Dispensing Provider provided kiosk, and an employee of a company in that office building can use a common MMS device at their office instead of the MMS device in their home. Such location independence avoids the problems inherent in the prior art when a patient forgets to take his medication with him when he leaves home as well as avoiding the problems resulting from forgetting to refill a prescription that has run out. Avoiding these problems reduces the chance that a scheduled dose will be missed or delayed.

In some embodiments, when a patient receives a medication from a Dispensing Provider other than their "home" Dispensing Provider, both Dispensing Providers communicate with other MMS Devices and/or Stakeholder systems of the MMS, that a patient's dose was received at an alternate location, and adjust their medication management records, reminders, and re-ordering appropriately. If communication means are not immediately available, the Dispensing Providers can alternatively communicate at a later time, utilize a store-and-forward approach, communicate the information to the patient's MMD device for relaying, and/or write a copy of the communication to a memory device for manual conveyance by the patient, Maintenance Provider, Provisioner, or other appropriate Stakeholder. The provision of alternative sources of medication dispensing with integrated record keeping provides an effective mechanism for managing a patient's medications.

In still other embodiments, the MMS system does not limit a patient to a pre-dispensed supply of medication and enables a patient to obtain their desired medications at any Dispensing Provider they can access which stocks the required supplies. A patient's MMS device can carry with it a copy of a digital "e-prescription" or references to an entry in an MMS Stakeholder's database that can be used by a Dispensing Provider. In some embodiments, the patient must authenticate themselves to the Dispensing Provider's MMS device in order to receive their medications. A Dispensing Provider's MMS device can then update the MMS Stakeholder's database on behalf of the patient, recording such information as doses dispensed, over-the-counter medicines and nutraseuticals purchased, etc.

Some embodiments provide further efficiencies through enabling the stocking of medications based upon various stocking models by connecting Dispensing Providers through the MMS Communications and Networking System. As mentioned earlier, pharmacists are increasingly stocking only the most common prescription medications in their pharmacies, and relying upon "just-in-time" logistics to deliver other medications to the pharmacy as need arises. This pharmacy-stocking model is, in essence, a caching algorithm that does not account for rarely used drugs or for spikes in demand such as would be encountered during a disease outbreak. As with all caching algorithms, improper use of caching leads to shortages that restrict patient access to medications. Because each pharmacy is independently operated for profit and relies upon consumer apathy and habit to enable the delayed just-in-time delivery of medications, there is increasing end-consumer dissatisfaction with current pharmacy caching models. Furthermore, mail-based pharmacies further erode end-consumer loyalty for regularly prescribed medications. Similarly, when a patient fills a prescription at a Pharmacy or visits a retail establishment to purchase over-the-counter medicines and/or nutraseuticals, and the Pharmacy or retail establishment does not have sufficient items in stock to meet the patient's needs, the end-consumer loyalty is further eroded. Thus, pharmacy-based dispensing models are vulnerable to consumer hoarding (e.g. caching by patients) which is designed to overcome the deficiencies caused by the combination of pharmacy-based caching and refill limits enforced by pharmaceutical management companies. Consumer fears, such as during the anthrax outbreak of 2001, have caused massive hoarding by patients of key drugs. Current prescription/pharmacy caching models enable this hoarding and the subsequent depletion of publicly available medications.

As will be understood by persons having ordinary skill in the art, connecting Dispensing Providers to other aspects of an MMS offers several benefits in this instance. As Dispensing Providers can provide doses one at a time to each patient, hoarding of medications is slowed or eliminated. The number of "vacation doses" (doses dispensed well ahead of the time they are to be administered in expectation of the patient not having access to an Dispensing Provider at that time) can be further limited, and in the case of a widely distributed Dispensing Provider network, largely eliminated. The convenience factor of being able to obtain the medications needed at the vacation location permits patients to avoid worry about vacation doses or stocking up on their medications prior to departure, or issues with customs, airline security restrictions, or other concerns. In addition, if the Dispensing Provider that a patient is attempting to use is out of stock for a specific medication, the patient can be immediately notified of the location of the nearest accessible Dispensing Provider that has stock of the needed medication. Alternatively, the Patent can be pre-notified of the location of a Dispensing Provider that has the necessary needed medication(s) in stock. When necessary and permissible, the patient can be provided a partial set of medications with the partial fulfillment noted in their electronic medication records, which can be shared with each Dispensing Provider that a patient interacts with so as to allow dispensing the remaining medications at another Dispensing Provider. Also, as the patient's usage is tracked by an MMS, their regular providers can be provided suggested stocking levels based upon anticipated demand for the item. Thus, if a patient is using the last of a particular nutraseutical, that patient's near-term expected purchase can be added to the expected demand by their provider. In some cases, the provider will be notified in a patient specific way (e.g., Ms. Smith is running out of Aspirin), and may use the opportunity to sell Aspirin to Ms. Smith in their next retail encounter. In other cases, the provider may simply adjust their stocking level if anticipated demand for a product is expected to be higher or lower than their normal stocking levels.

A connected system of MMS Devices offers other advantages. A patient or a set of patients can designate one or more specific Dispensing Providers as their "home" Dispensing Providers. These Dispensing Providers are located at convenient places the patient frequents very regularly, such as an office, a clinic, or a pharmacy. Designating "home" Dispensing Providers allows certain efficiencies in selecting the medications that will be cached at those specific Dispensing Providers. Specifically, each medication that a patient is prescribed, along with self-identified non-prescription medications, can be cached at the patient's "home" Dispensing Provider(s). The caching levels are determined by a variety of factors, as described below. Publicly accessible Dispensing Providers can be designated as "home" Dispensing Providers by one or more patients, allowing such Dispensing Providers to ensure an adequate supply of medications to meet the needs of these patients. In cases where a Dispensing Provider is not designated as a "home" Dispensing Provider for a patient, the Dispensing Provider's cache of medications will be based on typical past request patterns, expected future request patterns as determined by recent prescriptions issued in the area, area demographics and other factors, and the medications cached in nearby Dispensing Providers, but will not necessarily match the needs of a particular patient's prescription. Designating "home" Dispensing Providers permits better caching patterns, which will reduce patient effort in obtaining required medications, and increase the likelihood of their being taken on schedule. In some instances where a patient is on vacation or is admitted to a hospital for several days, a "home" Dispensing Provider designation can be transferred temporarily to another Dispensing Provider (e.g. a Dispensing Provider administered by the hospital, or one at their relative's house, or a Dispensing Provider at a hotel, resort, or cruise ship). The transfer can be made effective on a specific date, and optionally can require confirmation by the patient at the destination Dispensing Provider within a specific time. Alternatively, a patient can interact with a specific Dispensing Provider and change their "home" designation to that Dispensing Provider upon arrival. The transferal of "home" Dispensing Provider status can cause a change in the number and types of medications cached in the Dispensing Providers so designated. The MMS is operable to change the caching locations of the medicines "cached" in various MMS devices as described herein.

An MMS system is also advantageous for the management and dispensing of medication samples provided by pharmaceutical companies. In the US today, pharmaceutical company representatives deliver samples to physicians, who in turn dispense these samples to patients. The management and control of these samples is a burden on the physicians. Within an MMS, a Physician can provide a patient with an e-prescription in machine readable form, such as in the form of a credit card (like a debit card) or a storage device (such as a USB "thumb" drive), as a communication to any MMS Stakeholder, or as a record or set of records in an MMS Database, or in any other applicable form. The patient can fill the e-prescription at any Dispensing Provider stocking the prescribed medications. In some embodiments, automated dispensing machines can be provided by Dispensing Providers. These automated dispensing machines can dispense single or multiple doses of a medicine to a patient and record (or cause to be recorded) these actions in an MMS database.

In some embodiments, an MMS Device provides at least a basic set of capabilities to function as part of an MMS, and can include additional optional capabilities as determined by the function of the MMS Device within the MMS. The basic capabilities can include both software and hardware aspects. In more specific embodiments, basic MMS Device software capabilities include, but are not limited to, a device operating system, which controls the device hardware and other software, communications software capable of interfacing with other aspects of the MMS using one or more methods used by the MMS Communications and Networking system (which can require capability to cryptographically "sign" data and/or encrypt data for transmission and decrypt it upon receipt), and interfaces to optional MMS Device software.

In some embodiments, optional MMS Device hardware is used to extend the basic MMS Device hardware capabilities as part of creating a device capable of serving one or more particular purposes within an MMS.

Optional MMS Device hardware can include, but is not limited to, user interface components (e.g. screen, keyboard, mouse, touchpad, microphone, joystick, button(s), speaker (s), image input, etc.), non-medical sensing devices (e.g. RFID reader, laser or visual barcode scanner, image capture device, and/or fingerprint reader), medical sensor devices (e.g. blood pressure reader, heart rate monitor, body temperature sensor, breath analyzer, and/or blood analyzer), material handling equipment (e.g. medication storage, maintenance, concocting, packaging and dispensing devices, labeling systems, biomedical sampling and/or packaging systems), and/or security devices (e.g. alarms, lights, locks, access controls, seals, cameras, and/or armored containers).

In more specific exemplary MMS embodiments, MMS Devices are designed as collections of separate modules, each module supplying some capability required of the particular MMS Device. Individual modules can provide, without limitation, capabilities such as computer processing, data storage, communications interfaces, sensors and sensor management, material handling, security, environmental control, user interfaces, and/or power management. Modules are integrated during the design of the MMS Device in some exemplary implementations, while in others the modules may be designed in such a way as to allow re-configuration of the device to allow it to be upgraded in capability, repaired, or otherwise reconfigured. Such a modular design allows MMS Devices to be more accurately configured for their intended use, simplifies and reduces cost of maintenance, and permits addition of new capabilities as technology advances.

Possible embodiments of exemplary MMS Devices, including the broad categories of Medication Management Device (MMD) and the Medication Dispensing Device (MMS enabled device for dispensing medications, preferably at a Dispensing Provider) are described below.

6.2.3 MMS Communications and Networking

To permit an MMS (2500) to function, it is necessary that the various Stakeholders, MMS Devices and other aspects of the MMS be able to exchange data, alerts and other information. Such exchanges may be done in real-time, on a periodic basis, or an as-needed basis, as determined by the requirements and capabilities of the particular MMS, and make use of a variety of communication technologies and methods. The collection of hardware, software, procedures, methods, practices and systems that permit such exchanges in an MMS is referred to as the MMS Communications and Networking System (2400).

Communication can take multiple forms and consist of various technologies simultaneously or over time, as determined to be appropriate by those having skill in the art. These communication methods can, without limitation, provide peer-to-peer (P2P) communication, client-server communication, broadcast (one-to-many "push") capability, routed packet network capability, connection-oriented or connectionless protocols, redundant paths, store-and-forward capability, or direct linkage between devices. A variety of communication methods can be used in an MMS. For example, in some embodiments, aspects of the Medication Management System (2500) are configured to send alerts and notifications to patients using various communications devices and services (e.g., pagers, wireless devices, telephones, personal digital assistants) so that patients can receive such alerts and notifications using whatever means they desire. In such cases, certain MMS Devices are updated and coordinated through the MMS so that false alerts and notifications are not generated, such as when a patient receives their medications from a Dispensing Provider other than a designated "home" Dispensing Provider and uses that Dispensing Provider to update their compliance data. The patient's home Dispensing Provider, and other devices, such as the patient's portable MMD, would be updated with the compliance information and could cancel any associated pending alerts that might have been scheduled with respect to the particular dose of medication. Without the required communication means, the coordination and functioning of the MMS would be limited and management of patient medications would be impaired.

The physical communications means employed can include any of wireless (e.g. IR, WiFi, Cellular networks (e.g. GSM or CDMA), and Bluetooth) or wired (e.g. serial or parallel data cable, USB, device cradle with data connections, Ethernet, and token ring) communications means. Pre-existing networks, such as the Telephone System, Internet, private Intranets, and others can be used.

In some embodiments, an MMS Communication and Networking System allows for bi-directional message exchange between various MMS Devices and Stakeholders, using multiple protocols, with a business appropriate level of reliability and security. In more specific embodiments, the MMS Communications and Networking System is capable of dealing with unreliable or intermittent connection, such as can be encountered with cell phones connections in large buildings, underground structures, or in rural areas. In still other more specific embodiments, the MMS also has the capability for both one-to-one and one-to-many communications links to allow direct exchange of data between two parts of the MMS (e.g. for queries, data uploads, software update downloads, or other purposes) or broadcast of data to many parts of the MMS (e.g. to send system status updates, product recall notices, or other information of general interest to multiple MSS participants). Those having skill in the art will be familiar with appropriate technologies to implement this requirement.

Figure 2C:
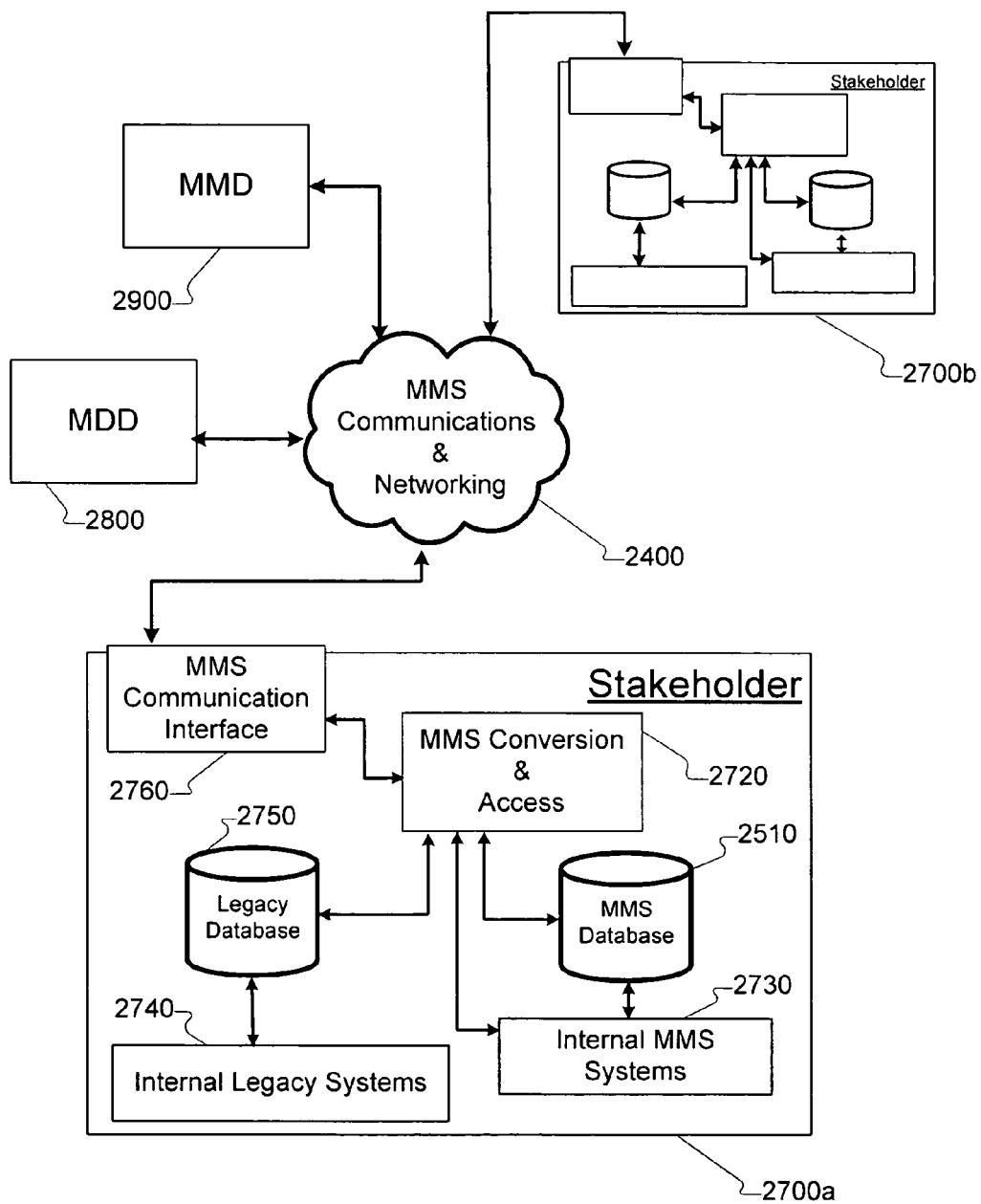

In some embodiments, the MMS Communications and Networking System are configured to enable allowed application programs to be written to manage data communication (not just voice) to and from the device so that more advanced functionality can be enabled in the device. Such applications can communicate with other devices, such as networked computers and other electronic equipment (including other wireless devices). Examples include the ability to send and receive email; review and process calendar, tasks, contacts, and other personal information manager records; retrieve, display and manage stock data; find and display nearby restaurants or clothing stores; and to receive or send documents and files using a mobile wireless device. Alternatively, these applications rely upon an always-available Internet connection, and communicate using standard Internet techniques and protocols (for example, sockets, UDP (User Datagram Protocol), TCP (Transmission Control Protocol), and HTTP (HyperText Transfer Protocol)). Each of these methods relies on the wireless connection's being available when needed. The use of SMS/MMS communication allows for a "push"and "pull" system. Critical information can be "pushed" out to subscribers via SMS/MMS messages (e.g. a product recall or the need for a patient to schedule an appointment with a Caregiver based on previously collected monitoring data), and the efficiency of a "pull" system can be used where an MMS Device also can poll the MMS on its own time schedule, or when its internal data buffers require refreshing (e.g. when the MMS Device was out of a coverage area, and it has updated information on compliance to send). Custom protocols also can be used. In some embodiments, at least some of the communications, are secured through industry standard cryptographic means and procedures well understood to those skilled in the art (e.g. AES cryptography, with Diffie-Helman style dynamic key exchange). These networking and telephone technologies are indicated in FIG. 2a, 2b, and 2c by the communications method clouds, and depicted in FIG. 3.

In some embodiments, these communication and networking capabilities are used in an MMS to facilitate MMS functions, such as, without limitation, prescription management, medication dose scheduling and recording, information queries, data transmission, and Stakeholder communication. The wireless nature of these devices permits their use even by patients and other Stakeholders whose location may vary constantly and where a fixed-location device would not be optimal. In additional embodiments, other technologies such as UnP (Universal plug and play), and communications standards such as HTTP and SSL, allow for communication with a great variety of devices through the MMS Communications and Networking System, whether these devices were designed specifically for use in an MMS or not.

Figure 3:
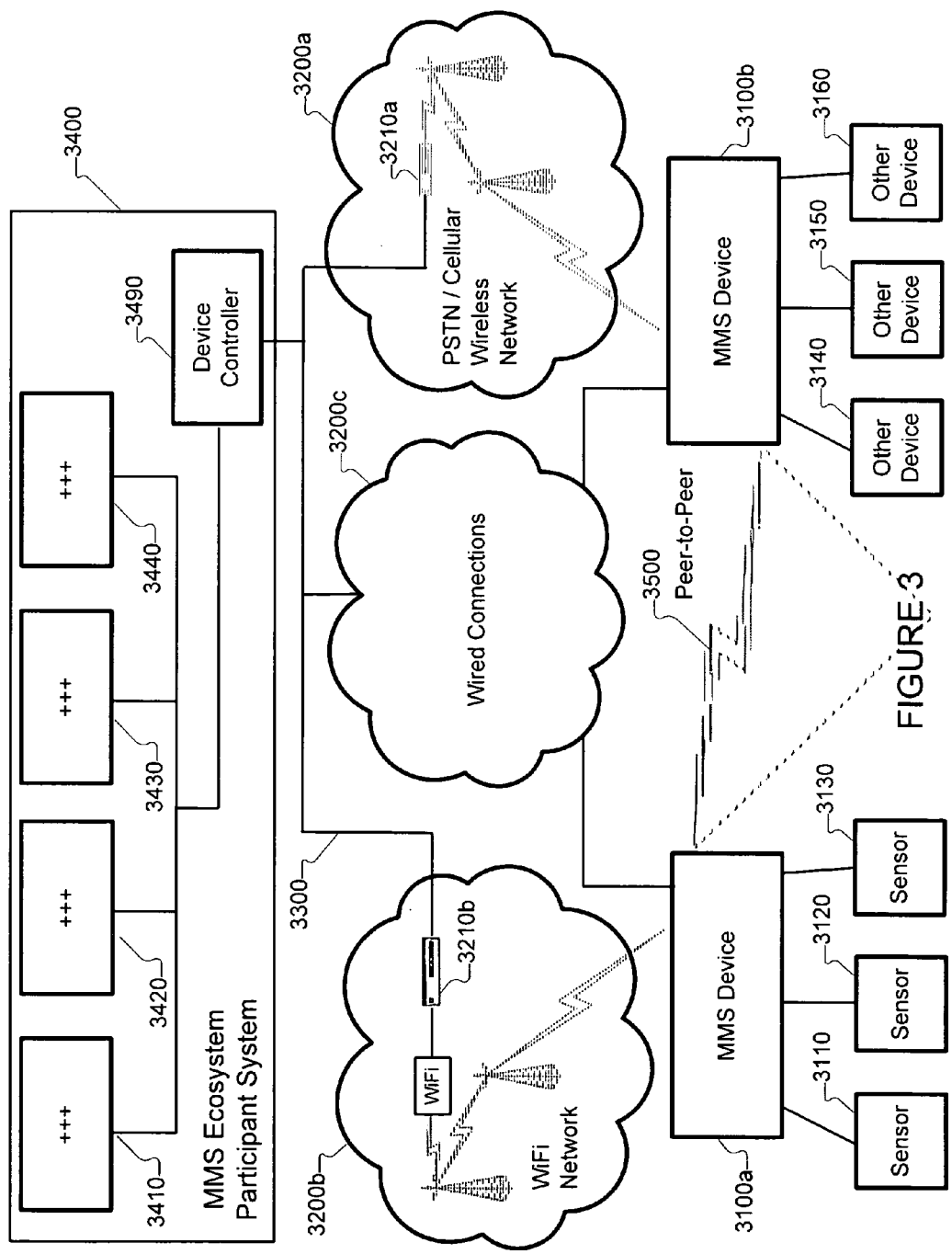
FIG. 3 depicts an exemplary communication system architecture.

FIG. 3 illustrates an exemplary MMS Communication and Networking System architecture in which a first MMS Device (3100*a*) communicates with a second MMS Device (3100*b*) or with the systems of any Stakeholder (3400) as necessary, in accordance with one embodiment of the invention. Either or both MMS Devices can be a wireless device or a wired device or be capable of both wired and wireless communications (e.g. a PDA, laptop or desktop computer, cell phone, etc.). Each MMS Device can communicate through one or more wired or wireless communications networks (e.g. 3200*a*, 3200*b*, 3200*c*) that each includes a gateway (3210*a*, 3210*b*) that is in communication with a computer network (3300) or through wired or wireless Peer-to-Peer (P2P) methods (3500). Examples of wireless communications networks 3200*a* and 3200*b* include cellular telephone networks utilizing CDMA (Code Division Multiple Access) or GSM (Global System for Mobile communications) technologies including wireless metropolitan or area networks utilizing 802.11-based technologies. Examples of Peer-to-Peer communication methods (3500) include Bluetooth, IrDA, and USB. Both wired and wireless communications networks (3200*a/b*) as well as Peer-to-Peer communication methods use components having designs, materials, and methods well known to those having ordinary skill in the art.

6.2.4 MMS Database

In some embodiments, data necessary to each Stakeholder's proper participation, and the proper functioning of the various MMS Devices, is maintained, safeguarded, and available to each entity that needs such data in a manner that protects the data integrity and confidentiality, while permitting all uses to be tracked for future reference (a "secure audit trail"). In one embodiment non-transient data is kept in the MMS Database (2510). The information can be kept in a central repository that is replicated as needed for access and limiting of outages, kept in a distributed form with different kinds of information kept in separate data repositories, a combination of the two, or any other arrangement which is appropriate to the requirements of the system as determined by those skilled in the art. Different Stakeholders can implement different information handling systems, but through the use of standardized protocols and data structures, interchange of information is possible. The distribution of data to the entities or devices that need it can be in "real time," or on a periodic or other basis as determined by, and done according to techniques known to, those having skill in the art.

In other embodiments, personal medication records stored within such an MMS are further replicated and stored in one or more locations; for example, within one or more MMS Devices. For example, a Dispensing Provider designated as a "home" Dispensing Provider for a particular patient can be further used to store medication and other medical records for that patient, and can provide those records to the MMS as required, or use the information to perform its functions, such as by checking patient allergies against a prescribed medication, or comparing all prescribed medications for the patient to check for interactions, and alerting the patient to any issues discovered so as to prevent adverse reactions. The provision of medical information with local caching of information in a peer-to-peer topology overcomes issues with service denial when connection to a central database is intermittently not available.

In still other embodiments, the MMS Communications and Network System is operated in an "unconnected" state, in which e-prescriptions, or other data, are delivered on physical media (such as a USB "thumb" drive); and Dispensing Provider data (such as re-supply orders for stocks of medications) is collected by service personnel during regular visits and uploaded to the MMS Database later. This capability allows provision of MMS Device functionality in areas where MMS Communications and Networking service is not available, or not available at times, such as may be the case in remote locations or during the times following natural disasters.

6.2.4.1 Types of MMS Data

In some embodiments, the proper functioning of the MMS, and in some cases compliance with various laws such as HIPAA (the Health Insurance Portability and Accountability Act of 1996), requires that data be available only to those who are authorized to have it, and that only those authorized to make changes to it be permitted to do so. Some data is highly confidential (such as patient medical records or biometric authentication data) and should be available only to those who have been authorized to have it, while other data is public knowledge (such as contact information for providers or service companies, or the locations of public-use Dispensing Providers), while still other data should not be generally available, but can not be considered legally confidential (such as service histories for equipment, or network addressing information for various devices). Some data is transient, some permanent, and some with other characteristics as determined to be proper by those having skill in the art. These requirements lead to a general classification of the kinds of data an MMS is configured to deal with, and some general guidelines for dealing with each. The kinds of data an MMS handles includes, but is not limited to, Authentication, Authorization, patient, Stakeholder, Infrastructure, and Integrity Tracking. Exemplary descriptions of each of these data types is described in the following sections; however, persons having ordinary skill in the art will understand that other descriptions for these data types, and other data types, can be provided without departing from the scope of the invention.

6.2.4.1.1 Identification and Authentication Data

Identification and Authentication Data consists of all data used to verify the identity of any person, system, or device interacting with an MMS. Such data can be stored for reference against supplied information when authenticating, be in transit from one part of an MMS to another, or be in the process of being collected at the point of authentication. Authentication data must be protected against unauthorized use or access at all times. This can be done through use of encryption, shielding, valid-time limitations, view-limiting devices, data hashing, or any other appropriate techniques known to those skilled in the art.

The Authentication Data can consist of passwords, "PINs," biometric data, interaction patterns, synchronized hardware "keys," explicit permission of an entity already authenticated and authorized to do so, any other method judged to be sufficiently secure by those skilled in the art, or by any combination of these.

Each MMS Device can store one or more sets of Identification and Authentication Data for a specific patient to permit the MMS Device to communicate with various Stakeholder systems of an MMS.

6.2.4.1.2 Authorization Data

Authorization Data specifies what actions are allowed for each entity or system that makes up or interacts with an MMS. These can include, but not be limited to, MMDs, Dispensing Providers, Stakeholders and their systems, other MMS Devices, or anyone with access to each of these. Authorization Data limits actions to those that are necessary to perform the role of the entity in question with respect to the proper functioning of the MMS. Actions can include querying, updating, or deleting data, adding, modifying or removing hardware or software components, performing supply, maintenance, or monitoring of any part of the MMS, granting, changing, or removing authorization for any entity or system, or any other actions which can be deemed to require authorization by those skilled in the art or as required by law.

The results of all authorization requests, along with other relevant data (e.g. the time of the request, what access was requested, who or what requested it, etc.), should be considered to be Integrity Tracking Data, and added to the secure audit trail.

6.2.4.1.3 Patient Information

Patient Information consists of all personally identifiable data (i.e. can be linked to a particular person, directly or indirectly) relevant to any patient. This can include, but is not limited to, name, address, medical history, social security number, insurance information, providers used, prescriptions, MMS devices used, Dispensing Providers used, biometric data (which also can be Authentication Data), compliance history, medication schedules, current location, or financial data.

Patient Information is considered confidential in all cases, and confidentiality can be required by law in some cases. Laws such as HIPPA require patient permission before certain information can be disclosed, and can place limitations on what can be disclosed, when it can be disclosed, or to whom it can be disclosed. An MMS must comply with all such requirements at all times and be designed to avoid accidental or intentional circumvention of these requirements. The use of Authentication and Authorization data can be used, in conjunction with other technologies such as encryption and digital rights management (DRM) to meet this requirement.

6.2.4.1.4 Stakeholder Information

Stakeholder Information consists of information that identifies, permits communication with, or describes businesses or other entities that make up or participate in the MMS. Such entities can be Caregivers, Pharmacists, Insurers, device maintainers, Hospitals, or other entities or any others that are necessary to the proper functioning of an MMS.

Stakeholder Information can consist of names, postal mailing addresses, street addresses, e-mail addresses, web addresses (URLs) and/or the associated web pages, phone numbers, FAX numbers, maps, directions, employee directories, IP addresses and port numbers, Internet domain names (DNS names), business forms, schedules, standards documents, periodic publications, or any other information which facilitates interaction between Stakeholders, or the various hardware and software systems of an MMS.

Stakeholder information should not include any information that is considered confidential. In many cases the information is publicly available, or even advertised (such as corporate names and mailing addresses). In some cases, the information is not considered public and should be accessible only to authorized entities within the MMS (such as IP addresses and port numbers, or maintenance schedules) to limit abuse or interference with the functioning of the MMS. Even for non-public information, however, there should be no legal requirements for confidentiality.

6.2.4.1.5 Infrastructure Information

Infrastructure Information consists of data that is used by an MMS to implement its functionality. This data can be ephemeral or permanent. This can consist of data packets in transit (possibly consisting of protocol information as well as the MMS data being transferred), routing information (e.g. routing tables or Address Resolution Protocol (ARP) information), program code (whether in source form or executable), data representations on display devices, or any other information needed to cause MMS hardware and software systems to perform their tasks, as well as any copies or derived versions of this data that can be created for update, repair or maintenance purposes (e.g. memory dumps, network sniffer traces, or notes made by maintenance personnel that includes MMS data).

Other exemplary types of data which can be considered as Infrastructure Information include, without limitation:

- Informational databases, such as medications databases used for checking potential interactions or for informing Stakeholders as to the uses, appearances, costs, side effects, or other attributes of medications.
- Maintenance diagrams for various MMS Devices for use by technicians working on such devices.
- Communications and Networking topology descriptions for the MMS, showing the connections available between Stakeholders and/or MMS Devices in the MMS.
- Current Status of MMS Devices, Communication and Networking connections, Stakeholders, and/or specific databases.
- Current list of spare parts, backup systems, redundant Communications and Networking paths, and their whereabouts and the responsible party for each.

Because some kinds of Infrastructure Information can include any other MMS data types, Infrastructure Information should be considered confidential in any case where inclusion of confidential information is possible, whether or not such information is present in every case. For instance, a network sniffer trace that includes packet data should be considered confidential, even when data is encrypted or otherwise obscured, as it is possible that patient information might be present in the packets, but ARP information does not need to be considered confidential because it will include only information about routing packets on a given network. Even if a particular kind of data does not have to be considered confidential, it can be considered confidential if this is seen as appropriate by those skilled in the art.

Preventing access by unauthorized people or systems to Infrastructure Information can require software protections, such as encryption, physical barriers such as locked cases or vaults, software-controlled access systems, monitoring such as video cameras and security personnel, sensors to detect breaches, or other methods as deemed appropriate by those with skill in the art.

6.2.4.1.6 Integrity Tracking Data

Integrity Tracking Data is data that is collected about the functioning and use of an MMS that will permit forensic reconstruction of events at a later time. This can consist of audit trails showing time-stamped database transactions, infrastructure security alarm records showing breaches of physical security, video camera recordings, maintenance records, network outage logs, process log files, or any other data deemed necessary for reconstruction of past behavior or state of an MMS system by those with skill in the art.

Integrity Tracking Data must be maintained in a form that is not easily subject to alteration, is not subject to undetected alteration or destruction, and which will not degrade during the time period required. Examples of possible storage media might include reports printed on paper, CD-ROM or optical disks that are "write once," data archived to secured storage facilities, and/or any other method that meets the requirements for provable authenticity, integrity, and appropriate longevity. Multiple copies can be maintained in separate locations and/or using different forms of storage to aid in meeting these requirements.

The various types of data used by an MMS can be complex and voluminous. Some already can be in use by various Stakeholders, using database and data management systems purchased commercially or developed specifically for the particular Stakeholder, or a combination of these. An exemplary MMS can implement its own database and data management systems, make use of existing commercial or Stakeholder systems, or a combination of these through the use of data conversion and connection systems. The data can be stored in a central repository which is accessed by all parts of an MMS having need of and permission for such data; it can be replicated from a central repository as needed and similarly accessed; it can be stored in a distributed manner with different types of data stored in different repositories, or repositories can be divided in any manner found to be acceptable to those having skill in the art. However the data is stored, sufficient means must be present to meet the requirements for data integrity, security, access, as well as access and update tracking.

Aspects of a possible exemplary MMS Database architecture are depicted in FIG. 2c. In this exemplary architecture, various Stakeholders (2700a, 2700b) and MMS Devices (2800, 2900) are connected through the MMS Communications and Networking System (2400) such that the MMS Communication Interface (2760) of each can exchange any required MMS data. Stakeholders can have legacy database systems (2750) in use that contain data relevant to the MMS, or which need to access MMS data, but which are not specifically designed to work with an MMS. They can have internal procedures or systems that are dependent on these legacy database systems, and which cannot be converted for various reasons (e.g. time, cost, lost source code, limited remaining useful life, etc.). They also can have database systems that are designed according to MMS requirements (2510). To allow both legacy systems and MMS systems to access both MMS databases and legacy databases without requiring legacy systems to be modified to comply with MMS standards or MMS systems to be made aware of legacy system standards the MMS database system can employ an MMS Conversion and Access system (2720). This system accepts MMS standard interactions, and accesses the MMS databases and/or the legacy databases as necessary, performing whatever data conversions are necessary to cause the returned data to meet MMS standards. MMS Conversion and Access systems can be used on any Stakeholder system necessary, and can exist in various implementations as required for a particular example of an MMS. MMS Devices, such as MMDs (2900) or Dispensing Providers (2800) also would access required Stakeholder data through such MMS Conversion and Access systems in the exemplary system.

6.2.4.2 MMS Directories

In addition to acquiring, maintaining and securing MMS data, the MMS data components also can incorporate a directory function to allow information to be located by systems or Stakeholders having authorized need for it. Existing directory methods, such as the Internet Domain Name System (DNS), the Lightweight Directory Access Protocol (LDAP), or similar systems can be used, or directory methods and systems designed specifically for MMS use can be implemented, or an MMS can use any combination of these as deemed appropriate.

An exemplary MMS can have multiple directory services used for different purposes. An exemplary system can use DNS to facilitate communication between MMS Devices or to allow Stakeholders to access information through standard web browser technology, while using LDAP to access Stakeholder contact information and a custom designed MMS directory service to permit use of a patient ID to locate information on all Stakeholders providing service to that patient (e.g. the patient's Insurer(s), Physician(s), Caregiver(s), and "home" Dispensing Provider(s)). Still other exemplary MMSs can use a single directory service to serve all directory needs (e.g. use of DNS to locate a web server that provides search capabilities for the MMS Database).

6.3 Exemplary MMS Devices

As depicted in FIG. 2b, two types of non-limiting exemplary MMS Device are described: a Medication Management Device (MMD) (2100) and a Medication Dispensing Device (Dispensing Provider) (2200). These devices can appear in multiple forms, with different capabilities, within a single MMS, or all such devices within a given MMS can have identical functions, forms and capabilities, as is determined to be appropriate by those having skill in the art. More specifically, both types of device can include both the basic MMS Device capability requirements described in section 6.2.2 as well as additional optional MMS Device hardware and software components to permit them to fulfill their purposes within an exemplary MMS. More specifically, either type of device can be connected to the MMS through a wired or a wireless communication method, or through both, either simultaneously or at different times as needs, preferences, authorizations and capabilities determine. Any or all of these possible communication methods are represented in FIG. 2b by the "MMS Communications and Network System" cloud (2400). This system allows communication between MMS Devices and Stakeholders, MMS Devices and other MMS Devices, or between Stakeholders.

Basic MMS Device hardware capabilities can include, but not be limited to, computer processing (CPU, RAM, etc.), which are operable to execute MMS Device software, data storage (hard or floppy disc, flash memory, etc.), input/output devices (e.g. RFID reader, USB, Laser/Infrared, RF (e.g. Bluetooth, WiFi 802.11a/b/g/etc.), Firewire i1394, Serial RS-232, parallel port, telephone (e.g. v.32) or cellular (e.g. CDMA, GSM) wireless interface, etc.), interfaces provided as optional MMS Device hardware, and a power supply (e.g. battery, mains power, solar cells, chemical power, or electrical inductance).

An exemplary MMS can include additional types of MMS Device (2300) as determined by those having skill in the art. Such devices can incorporate some or all capabilities of the described exemplary MMD and/or Dispensing Provider-provided Medication Dispensing Devices, or they can perform functions dissimilar to both MMD and Dispensing Provider provided Medication Dispensing Devices, such as maintaining proper environmental conditions, security, and chain-of-custody for medications in transit with a Logistics Provider.

An MMS (2500) can deploy one or more MMDs (2110, 2120 or 2130, individually or in combination), which can be deployed in a variety of configurations and capabilities, which act as non-dispensing interfaces between a patient and the rest of the MMS. The MMDs (2110, 2120 and/or 2130), alone or in conjunction with a Dispensing Provider provided Medication Dispensing Device(s), allow for medication due alerts or other information to be communicated to a patient as needed, medication compliance data to be recorded and communicated to the MMS (2500), or for other uses consistent with the functioning and intent of the MMS (2500) as determined by those having skill in the art. Exemplary Dispensing Provider-provided Medication Dispensing Devices (2200) and MMDs (2100) are described later.

In some embodiments, an MMS (2500) is configured to automate many aspects of medication and compliance management. In more specific embodiments described below, the Dispensing Provider provided Medication Dispensing Devices (2200) are configured to provide a distributed mechanism for managing the dispensing of medications to one or more identifiable and authorized patient(s), while the MMDs (2100) act as an interface between the patient and the MMS for conveying alerts, compliance data, or any other appropriate MMS data to or from the patient. In still more specific embodiments described below, the Dispensing Provider provided Medication Dispensing Devices (2200) are configured to record the medications and dosages dispensed. In yet more specific embodiments, the MMDs are configured to record patient compliance with their medication regimen (s). In yet other embodiments, the medication compliance information obtained and generated by the MMDs is passed to one or more recipient Stakeholders (2600). MMDs (2100) can be used to assist with these processes by such methods as recording patient compliance with medical regimen, storing the information and relaying it to the MMS directly by its own means, through a Dispensing Provider provided Medication Dispensing Device (2200) when such is possible, or through such other means as can be determined to be useful and proper by those having skill in the art. The MMD also can be made capable of interfacing with patient monitoring equipment and relaying patient status information to the MMS (2500), or others as determined to be proper by those having skill in the art.

6.3.1 Exemplary MMD Architecture

FIG. 2*b* depicts three example embodiments of MMDs (2110, 2120 and 2130) communicating with various participants within an MMS environment through the Communication and Network System of the MMS. Each device is of a different type. Device 2110 is a programmable industry-standard wireless device (e.g. a cellular telephone) with an integrated RFID reader, running one or more MMD software components, as described below. Device 2120 is a combination device comprising an MMD software component running on an independent circuit board. Device 2130 is an industry standard microform personal computer with a variety of external interfaces, as described below.

Basic MMS Device (and thus MMD device) hardware capabilities can include, but not be limited to, computer processing means (CPU, RAM, etc.), which are operable to execute MMS Device software, data storage (hard or floppy disc, flash memory, etc.), input/output devices (e.g. RFID reader, USB, Laser/Infrared, RF (e.g. Bluetooth, WiFi 802.11a/b/g/etc.), Firewire i1394, Serial RS-232, parallel port, telephone (e.g. v.32) or cellular (e.g. CDMA, GSM) wireless interface, etc.), interfaces provided as optional MMS Device hardware, and a power supply (e.g. battery, mains power, solar cells, chemical power, or electrical inductance). Still other configurations will be apparent to persons having ordinary skill in the art.

6.3.1.1 MMD Hardware (3100)

Figure 4:
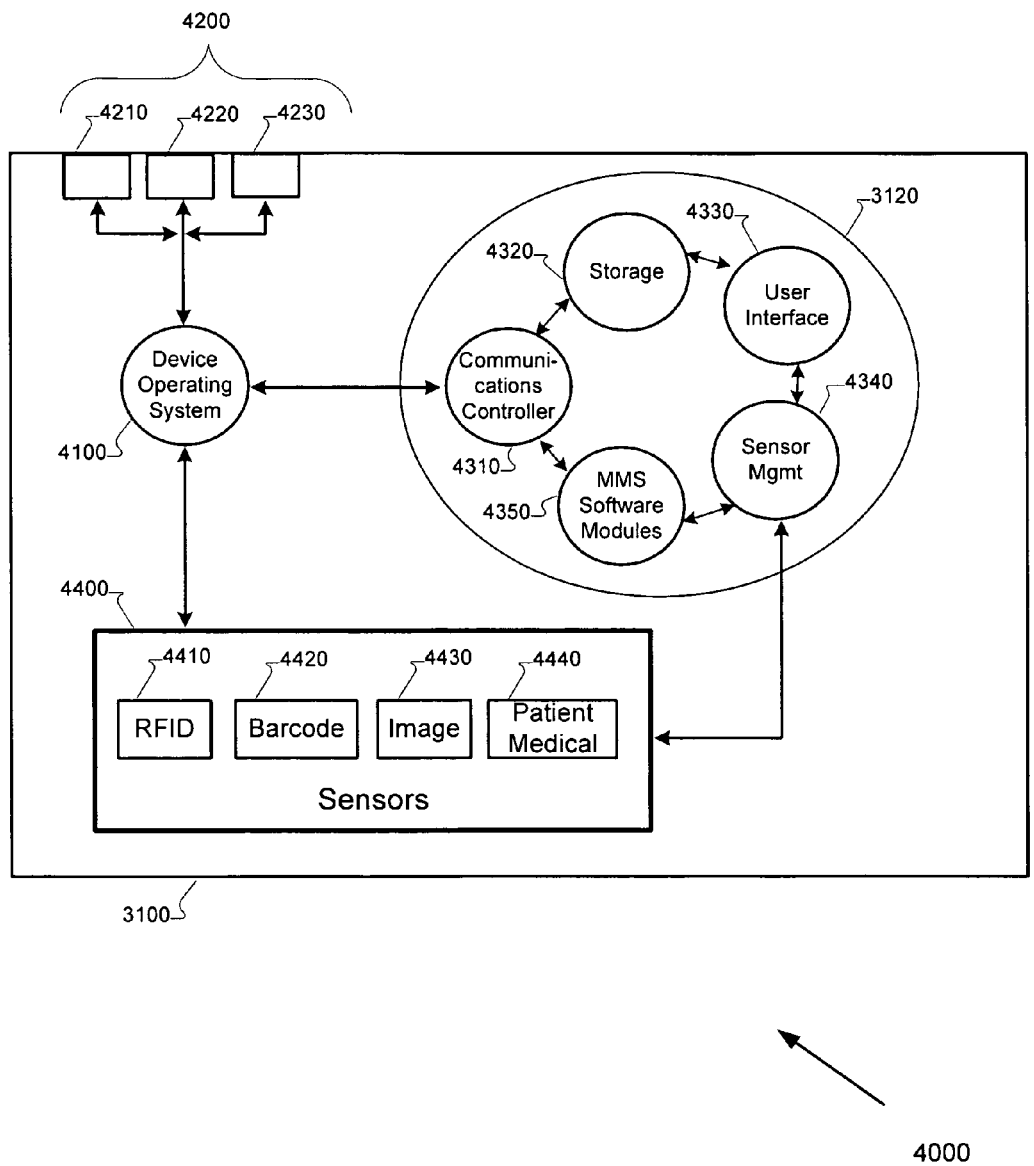
FIG. 4 depicts an exemplary architecture of a Medication Management Device.

An exemplary MMD (3100) is described in FIG. 4. An MMD (3100) can be implemented using purpose-built hardware, or using existing wireless or wired devices possessing the required basic set of capabilities as described above. Suitable wireless devices include pagers, mobile phones, and combination devices that include the functionality of mobile phones, pagers, and personal digital assistants (PDAs), or some combination of these devices. These devices can allow the exchange of textual information (e.g., pagers, cell phones, or PDAs) as well as voice and data (e.g., cell phones and PDAs). Wireless devices can incorporate useful features such as global positioning system (GPS) access, cameras, and scanners (including scanners able to process radio frequency identification (RFID) and barcodes), and removable data storage devices.

An exemplary MMD can alternatively be a purpose-built device with local CPU, power, storage, and communications. The MMD's CPU provides MMD processing of MMD software. Power can be supplied by a rechargeable battery, connection to mains power, built-in solar photovoltaic cells, or other system appropriate to the intended use pattern of the MMD. The MMD has RAM and FLASH chips to supply data and program storage capabilities. The MMD can communicate with the MMS Communications and Networking System via wireless or wired connections. In some exemplary devices the communication connection also may be used to supply power to the device, such as with a USB port. The MMD also can have an RFID antenna that can read product tags for the purpose of identifying medication packages and/or verifying their integrity.

Another exemplary MMD can be an industry standard microform personal computer running MMD software, with a variety of external interfaces, or it can be constructed in any number of physical configurations, using industry standard components or purpose-built proprietary components or any combination of standard and proprietary components as determined to be appropriate by those having skill in the art. The interfaces of such an exemplary MMD can fall into the category of contact or non-contact devices, wired or wireless, and be used for connection to the MMS Communications and Networking System or for other purposes, such as interacting with patient monitoring devices, such as heart monitors, blood pressure meters, as well as other devices such as alarm systems, which are not capable of interacting directly with an MMS. Examples of some of these interfaces are: Non-contact interfaces: RFID, Bluetooth, infrared, laser, wireless Ethernet or WiFi, or cellular telephone; Contact interfaces: wired Ethernet, USB (Universal Serial Bus), FireWire (i1394), serial interfaces (RS-232, USB), and telephone modem service. In some embodiments, a suitably-equipped MMD functions as a centralized home health unit, coordinating the functions of various communications devices, telemetry devices, and external communications functions such as alarm and response services, and feedback to medical and health professionals or other Stakeholders. This exemplary MMS Device (3100) includes a Device Operating System (4100) of standard construction known to those having skill in the art, including, for example without limitation, the WINDOWS, WINDOWS MOBILE, or WINDOWS CE operating system available from Microsoft Corporation, UNIX, LINUX, MACOS, SYMBIAN, RIMOS, and PALMOS, and NOS (Nokia Operating System). Still other MMS Devices cannot have an operating system per se, but provide, for example, an environment for running Java 2 Micro Edition (J2ME) programs, Binary Runtime Execution Environment (BREW) programs, or similar execution programs and environments.

In these cases, the execution environment is considered to be acting as the device operating system. Possible MMS Devices (3100) include cellular telephones from Nokia of Helskini, Finland and Motorola of Shamburg, Ill., and Blackberry devices from RIM of Waterloo, Ontario, Canada.

A Device Interface (4200) provides a means for converting data to signals compatible with a network (3300), another MMS Device, and/or other communication connection. The various components of the Device Interface (4210, 4220, 4230) can implement wired- and/or wireless communications protocols. An example of one such wired communications protocol is Ethernet. Examples of a wireless communications protocol include WAP, 802.11x, and telephony protocols for wireless telephones. The provision of a device interface (4200) to support satellite telephony technology is also contemplated. The selection and management of the device interface (4200) is made under the control of the Device Operating System (4100). Each device can be constructed with one or more Device Interfaces, which can enable the MMS Device to simultaneously communicate through multiple means, or to select the optimal means from several that can be available.

In some embodiments, the exemplary technology includes a peer-to-peer or client-server connection to a second device, which performs as a proxy between the MMS Device and aspects of the MMS (3400). The alternative technology provides for a proxy device, which can be an MMS Device as described herein, a server, or other computer system such as a desktop computer, a Dispensing Provider provided Medication Dispensing Device, or any other capable device. Alternatively, a network appliance such as a cable modem or set top box can be used as the proxy device. The proxy device provides control channel or other MMS information to be communicated to and from the MMS Device via the proxy device instead of communicating directly. Use of a proxy device is effective for bypassing firewalls and monitoring systems using peer-to-peer networks and protocols.

In one particular exemplary implementation, a peer-to-peer network connection can be constructed between the MMS Device (3100*a*) and the proxy device (3100*b*) using a peer-to-peer network (3500) such as Bluetooth, Infrared, or 802.11 technologies. Other wireless technologies can be used if they are supported by both the wireless MMS Device (3100*a*) and the proxy device (3100*b*). Control information and MMS data can be passed from aspects of the MMS (3400) directly to the wireless MMS Device (3100*a*), or can be relayed through a proxy device (3100*b*). MMS information can be passed directly to aspects of the MMS (3400), or can be passed to the proxy device (3100*b*) for forwarding to other aspects of the MMS. FIG. 3 shows an exemplary peer-to-peer network connection (3500) where Medication management information is passed from the MMS Device (3100*a*) through a 802.11 connection (3500) to proxy device (3100*b*), which then forwards the medication management information through PSTN/cellular wireless network (3200*a*) to network (3300) to aspects of the MMS (3400). Control or other MMS information also can be passed in the opposite direction through the network from one or more aspects of the MMS (3400) to the proxy device (3100*b*) and then to the MMS device (3100*a*).

Additional, optional, components are present in some other exemplary devices. These include, but are not limited to, sensors able to read industry standard RFID tags (4410), scan barcodes (4420), capture images (4430), read biometric data, and/or gather patient medical data, such as heart rate, blood pressure, body temperature, blood glucose level, or other such data (4440). Reading RFID tags can be useful in identifying medication packaging, verifying package integrity, or authenticating Stakeholders or MMS Devices. Reading barcodes can be useful in identifying packaging, inputting data, or other uses. Image capture data can be used to scan barcodes, identify medication visually, collect biometric data for authentication or other purposes, convey security information, collect medical information for use by Physicians or First Responders or other Stakeholders, or for other purposes. These devices are controlled by the device operating system (41 00) and the sensor management module (4340).

6.3.1.2 MMD Software

In some embodiments, MMD Client Software (3120) creates, manages, stores, and otherwise processes MMS Data and implements MMS processes appropriate to this type of MMS Device. It is comprised of MMS Software Modules (4350), which communicates with Communications Controller (4310), Sensor Management (4340), User Interface (4330), and, through the Communications Controller and by use of the Device Interface hardware, other aspects of an MMS (3400), such as Stakeholder systems or other MMS Devices. The MMD Client Software (3120) manages and coordinates the operation of the exemplary illustrative technology herein upon the MMS device (3100). The MMD Client Software (3120) can be referred to herein simply as the "client." In simplest form, the client (3120) sends and/or receives messages from aspects of the MMS (3400) through the MMS Communications and Networking System (3200), device operating system (4100), and at least one device interface (e.g., device interface 4210); manages the instructions and data encoded in the messages, and sends response messages back to one or more aspects of the MMS (3400) containing MMS Device information, user responses, additional commands, and collected information (again through the device operating system (4100) and the selected device interface (4210)). In alternative embodiments, the client (3120) acts upon the instructions encoded in the messages and downloads or causes to be downloaded, one or more modules for use in controlling or handling data from optional hardware components (4310, 4320, 4330, 4340, 4350) or to provide additional features and functions to the client (4310, 4330, 4350). This ability to download updated or new software allows the MMD to be adapted to changes in the MMS without requiring replacement of the device or specific action on the part of the device user.

In some embodiments, the User Interface (4330) of the MMD Client Software deals with all interactions with the device's users. The User Interface (4330) conveys information to the user in an appropriate form, such as text on a screen or through a Braille output device, audible tones or language through a speaker or other appropriate hardware, various lights or other visual indicators, or such other capabilities as the device might possess and support through the Device Operating System and/or MMD Software modules. The User Interface (4330) collects input from the user in various forms as determined by the hardware capabilities of the device. Possible input devices include keyboards, mice, joysticks, buttons, switches, sliders, microphones, touch screens, eye movement tracking devices, some combination of any or all of these, or other means as determined by those having skill in the art.

In other embodiments, the Sensor Management (4340) of the MMD Client Software deals with all interactions with the device's sensors (4400). It will monitor the sensors for input, collect and process the input for use by other components of the MMS Client Software or other parts of the MMS as required.

In still other embodiments, the Communications Controller (4310) of the MMD Client Software deals with all interactions between the device's other software and various aspects of the rest of the MMS. It makes use of the Device Operating System's capabilities to send and receive data through the Device Interface(s). As data is received, it passes it on to the appropriate part of the MMD Client Software for processing. As data is sent, it ensures that it is received by the appropriate part of the MMS.

In more specific embodiments, the MMD Software Modules (4350) of the MMD Client Software consist of various programs, functions, or other software that colectively implement the MMD's purpose within the MMS. The functions performed by these modules can include, without limitation, authenticating Stakeholders or MMS Devices, querying MMS databases, scheduling patient medication alerts, permitting patient interaction with other Stakeholders (messaging), recording patient compliance with medication regimens, holding collected information for upload to the rest of the MMS once communications become possible, or any other function of an MMD in a given MMS. In still more specific embodiments, the set of modules that make up this part of the client depend on the hardware capabilities of the device, the requirements of the user, and the capabilities of the particular MMS. For example, if a particular exemplary MMD has no patient sensing hardware, the modules that deal with patient sensor data cannot be present. If a particular exemplary MMD has no image sensor hardware, the modules that deal with biometric image data, barcode reading through image data, and image processing cannot be present. However, there is no requirement that unnecessary modules not be present, and there can be reasons, such as standardization, the economics of mass production, or hardware in modular form where additional capabilities could be added at any time, that might result in currently unnecessary modules being present. In such cases, the modules should be constructed in such a way that their lack of utility or inability to function in their intended role does not adversely affect the MMD's capability to perform its role in the MMS.

In yet more specific embodiments, the MMD software is written in an industry-standard language that is appropriate for the factory-provided operating system and hardware of the industry-standard wireless device. For example, MMD software for Palm devices is written using the Palm OS software standards, while MMD software for Nokia devices is written to the Symbian software standard. In some embodiments, the standards can be the same, such as when the MMD software is developed in the J2ME environment. In an exemplary implementation, when the MMD software is initially installed on a device, it checks to ensure that the device is a supported device with all of the appropriate hardware devices and communications abilities. The software then attempts to establish communications with the MMS environment via all possible support means to confirm communications. Once the most effective communication method has been established, the software then begins its synchronization with the MMS environment. At the first opportunity, the MMD software creates a local storage pool that maintains multiple days' worth of patient medication schedule data, or other appropriate MMS data such as network directories, authentication keys, etc., and the synchronization state of that data. This allows the software to operate under conditions of intermittent contact with the central operating system environment. The MMD software also interfaces with the device sensors, such as an RFID reader. If an RFID reader is present, the software performs an RFID synchronization with the MMS and then instructs the RFID reader to periodically scan its environment for any RFID tags associated with the MMS. Additionally, the software maintains a list of RFID tag prefixes in its local storage pool to ensure that it is only searching for a limited number of tags. The tag prefixes that are locally stored are constantly synchronized with the central environment in order to maintain close control of compliance information. This allows the storage pool to be limited in size as well as providing a number of crosschecks for the appropriate items to be maintained inside a control range. The RFID synchronization involves associating itself as a user/device pair, and then receiving from the MMS environment the RFID tag prefixes that it should respond to. It then activates the local RFID reader and searches for those expected RFID tag prefixes, and if found, stores their status in its local storage pool, and then communicates that status back to the MMS environment. If an expected tag prefix is not found, that information is also stored in the local storage pool and communicated back to the MMS environment. In this way a constant sliding window of expected tag prefixes and status codes is constantly maintained by the local device, with a full history of all associated RFID tags being maintained by the MMS environment. Alternatively, an automatically synchronized database can be used to store information and to synchronize with other systems and devices of the MMS. One such automatically synchronized database is provided commercially by Adesso Systems, Inc. of Boston, Mass.

In some embodiments, the MMD is a widely distributed MMS Device form, particularly in a wireless format, as sensor-enabled, third party programmable wireless devices become a global standard. As will be apparent to persons having ordinary skill in the art, such a development offers the user the greatest level of convenience for tracking and compliance data, as wireless devices are almost ubiquitously carried, and thus allow for almost real-time data to be collected and displayed. In various embodiments, an MMD device can be implemented in any number of form factors. These form factors include stand-alone items such as a belt clip device, or integrated items such as a branded cellular telephone holder, or incorporated into a fashion item; such as the company Coach does with ipod holders.

6.3.2 Exemplary Dispensing Provider provided Medication Dispensing Device (MDD)

Figure 5A:
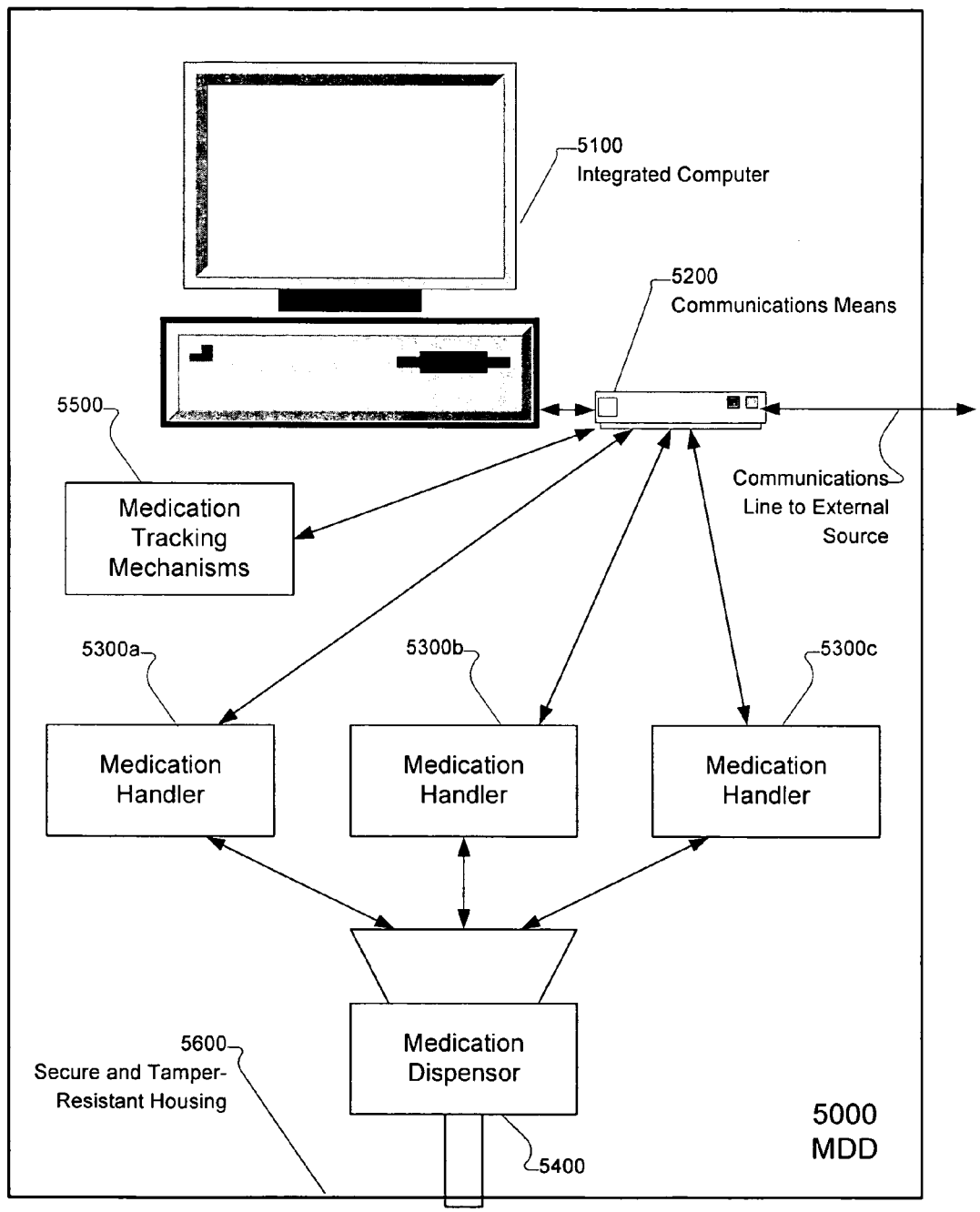
FIGS. 5a through 5c illustrate a Medication Dispensing Device (MDD) in accordance with the present invention.
Figure 5B:
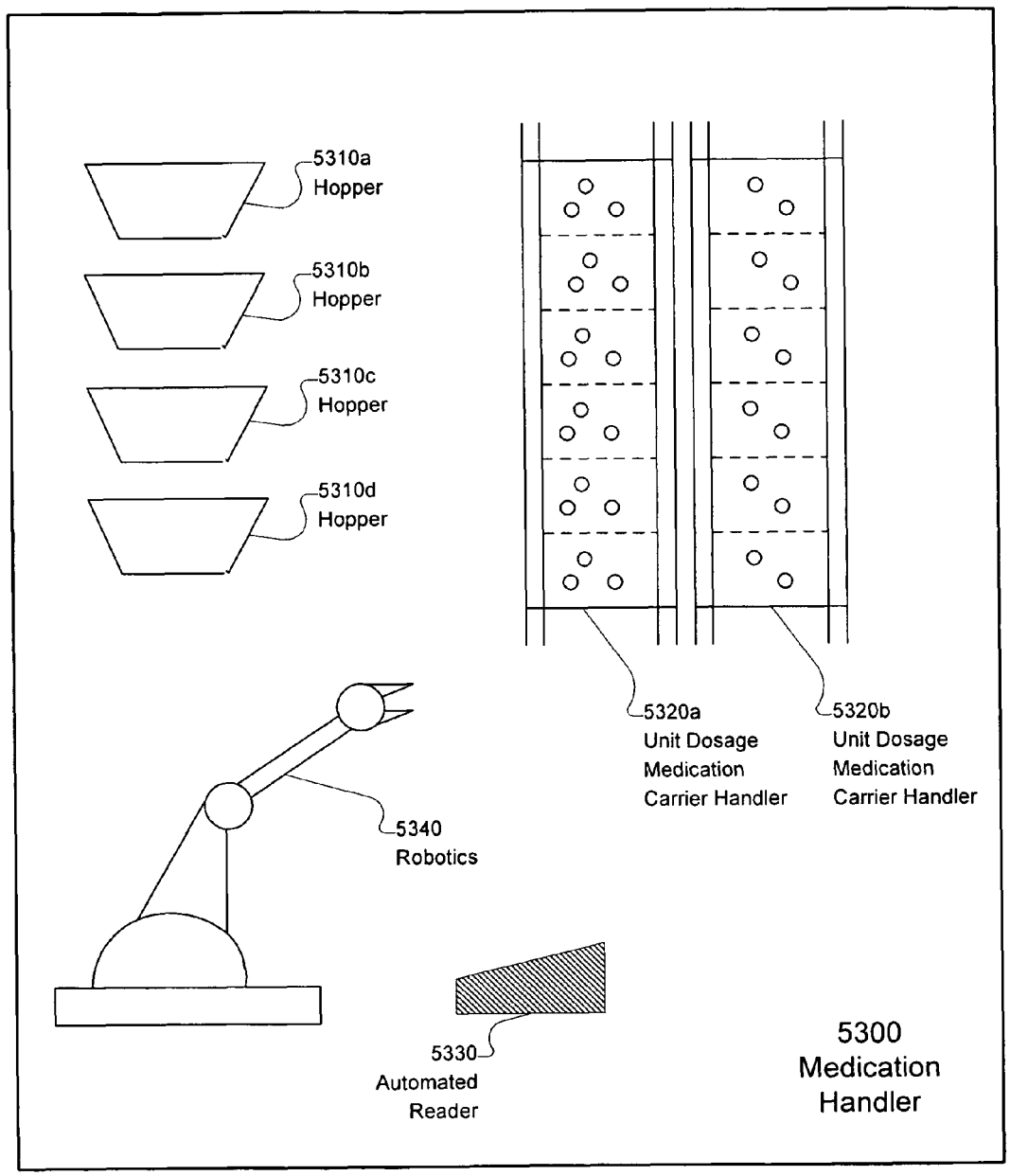
Figure 5C:
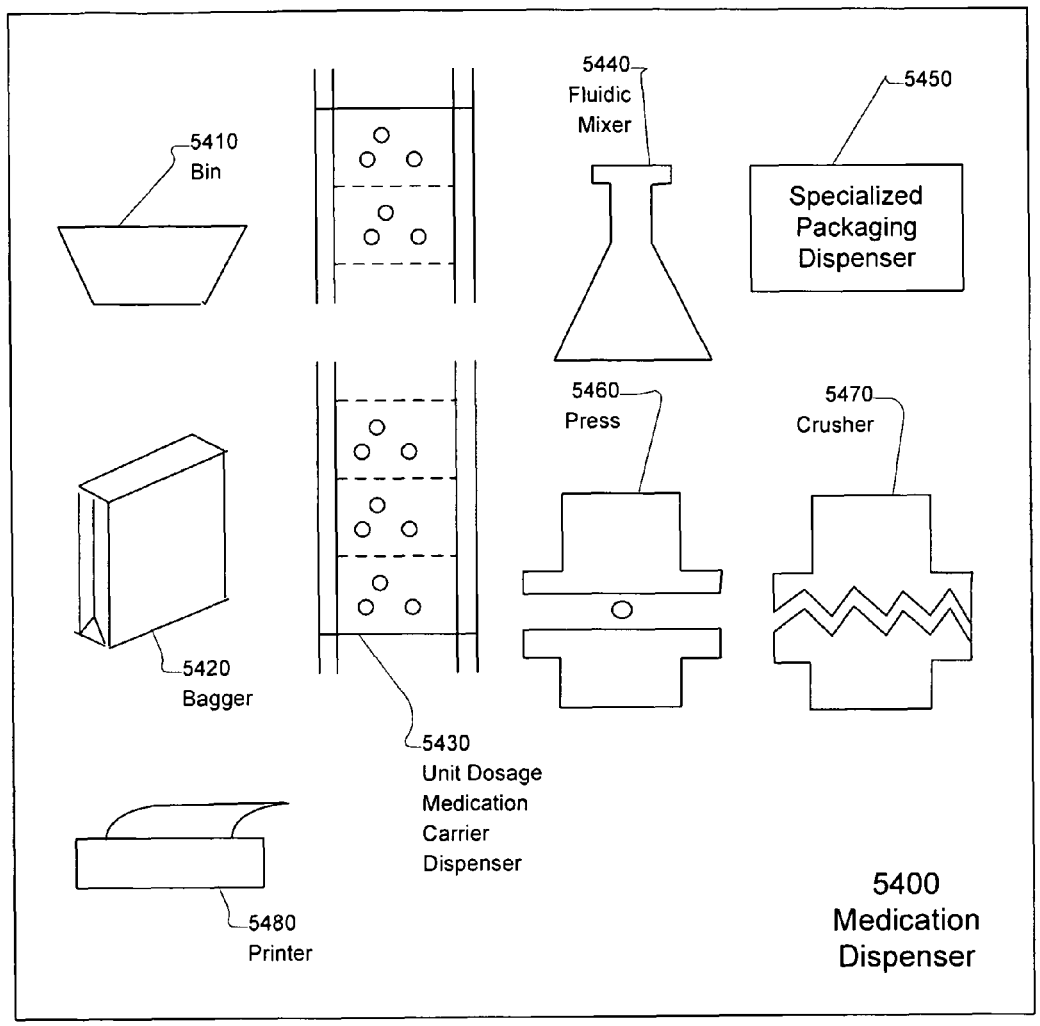

An exemplary architecture of an MDD provided by the present invention is illustrated in FIGS. 5a, 5b, and 5c. Referring to FIG. 5a, an MDD (5000) comprises, in the illustrated embodiments, at least one integrated computer (5100), an optional integrated communications means (5200), one or more medication handlers (5300), one or more medication dispensers (5400), one or more medication tracking mechanisms (5500), and a secure and tamper resistant housing (5600). Non-limiting exemplary embodiments of each of the components will now be described in greater detail.

The MDD's integrated computer (5100) is configured to provide medication management, tracking, and control of a patient's integrated medication record, as well as govern the mechanical operations of the MDD. In some embodiments, the integrated computer comprises standard computer components, such as a processor, memory (e.g., RAM, ROM, or flash), I/O controllers, and other means to control specific components within the MDD. An MDD further comprises at least one removable, machine readable/writable media interface, such as a USB port, magnetic card writer, CD or DVD writable device for reading and writing machine readable e-prescriptions and medical history information. The provision and configuration of such components will be familiar to those having ordinary skill in the art.

The MDD of the described medication management system provides for the dispensing of medications in patient-friendly packages, ranging from a single dose through multiple doses. Each MDD can be configured with a variety of dispensing options, ranging from simple pill dispensers, to pill presses that combine disparate medications into one or more personalized pills, to dispensers that automatically fill and label medication-dispensing devices. In some embodiments, Dispensing Providers can be configured to incorporate aspects of an MMD, and perform medication management functions as well as medication dispensing functions. In these embodiments, an MDD not only dispenses medications, but also monitors patient compliance, provides a means to access and update patient information or to alert the patient when medication is required, or when other information needs to be conveyed and/or any other functions of an MMD.

In more specific embodiments, the MDD's integrated computer further comprises software to manage the hardware of the MDD, its communications means; and still further comprises other software for managing and dispensing the medicines or other items at the Dispensing Provider. In other embodiments, the software is further configured to perform one or more of the following functions:

Manage stocks of medicine, including ageing, stock order/replenishment/transfer, and other functions.
Identify medicine interactions and report/notify the patient, Pharmacists, and Physicians when potential interactions are identified.
Perform patient management, including monitoring and reporting patient compliance with medication regimens.
Provide record management, including the protection and distribution of medication records and e-prescriptions.
Provide user assistance, in the form of help screens, and "live" chat with Pharmacists and medical personnel.

In still more specific embodiments, the MDD's computer hardware and software are tamper resistant. In still more specific embodiments, the MDD as a whole can incorporate tamper resistant features and/or include security monitoring and/or tamper-detection systems. The provision of the hardware and software capabilities and functions just described can be implemented using techniques known to those skilled in the art.

In other embodiments, the MDD includes one or more methods for working with the MMS Communications and Networking System as described above, whether through wired or wireless communication means, or both (5200). For example, an MDD can be plugged into a building or home network, or use a cellular phone network's Internet access capability. Embodiments of MDDs will provide at least the basic hardware requirements for the particular MMS and can provide whatever other capabilities are required to fulfill its function in the MMS.

The provision of the hardware and software capabilities and functions just described can be implemented using techniques known to those skilled in the art.

In some embodiments, within the described MMS (2000), each patient can obtain their medications at any Dispensing Provider (or Dispensing Provider provided MDD) that is stocked with medications that the patient is authorized to take. Furthermore, a Dispensing Provider (or their MDD) can include the functionality of an MMD so that each patient can update their medication compliance record at any such Dispensing Provider (or Dispensing Provider provided MDD). The MMS also can allow other interfaces to the patient, for example, through the use of Web browsers or other communications means such as SMS or telephony. The MMS will then update its records automatically and distribute those records within the MMS as required.

In still another aspect of the invention, the MMS (2500) of the invention is configured to function in a decentralized network, so that services can be delivered even during a partial or complete loss of network connectivity. Each MDD is configured so that it is capable of caching records, medications, e-prescriptions, and compliance reports during the duration of a network outage, and to accept and dispense medications during these outages. Each MMD is configured so that it is capable of caching records, e-prescriptions, and compliance data, as well as potentially other information, such as patient medical sensor equipment data, during network outages or other periods where communication with the required parts of the MMS is not possible until at least such time as communication is restored.

Referring back to FIG. 5a, the tamper resistant housing (5600) includes, in some embodiments, tamper detection circuits and one or more tamper alarms. The tamper detection circuits monitor the integrity of the tamper resistant housing, and report tampering to the Dispensing Provider computer monitoring them, which can alert a monitoring service so that appropriate action can be taken. The tamper detection circuits also can trigger a local tamper alarm. Provision of such features can be accomplished using methods known to those having skill in the art.

7 EXAMPLES

The following examples are provided to illustrate certain aspects of the present invention and to aid those of skill in the art in practicing the invention. These Examples are in no way to be considered to limit the scope of the invention in any manner.

7.1 Example Process for patient Filling a Prescription

FIG. 6 depicts an exemplary process flow for a patient filling a prescription in an MMS. The process begins 30 when an Authenticated and Authorized Physician enters a prescription into the MMS database for a patient (6110). The prescription is in the form of an entry into the MMS database. The database entry records all information required to identify the Physician, the patient, the medication and the dose size and schedule of administration, as well as any other information deemed proper by those having skill in the art. The MMS looks up the patient's medical history, and any other current or recent prescriptions, and checks for potential interactions or allergies (6120). If problems are found (6130), the Physician is informed (6132) and the prescription is rejected unless the Physician enters an override (6134). Audit records are created to record the action. Audit records are created to record each step of this process, as with each process in the MMS.

The MMS sends the medication and/or dose schedule data to the patient's MMD (6140), which sets up an alert schedule to notify the patient to take the medication at the appropriate times. The Dispensing Provider, or the Dispensing Provider's MDDs used by the patient, or those local to him, are informed about the new prescription (6150) and at least some of them take steps to ensure that appropriate stocks are available (6160). The patient uses his MMD to inquire about the location of the nearest Dispensing Provider that is capable of filling the prescription, the MMD does a query to a directory service for the information, the information is returned and the patient is given the information by the MMD (6170). The patient goes to the Dispensing Provider's location. At the Dispensing Provider, the patient uses his MMD, which has connected to the Dispensing Provider's MDD using Bluetooth technology, to Authenticate that he is an Authorized patient (6180) and request one or more doses of his new prescription. Once the Dispensing Provider has verified his identity, and that the Prescription requested is valid for the particular patient, and that all materials and supplies required to fill it are available, the Dispensing Provider retrieves and processes the appropriate medications and/or ingredients according to the prescription and packages them for the patient and dispenses the requested dose(s) (6190). How many doses are dispensed is a function of how frequently the medicine is taken, how close to an appropriate MDD the patient is in the course of the day (is it in his home or office, or does he have to drive 20 miles out of his way to get to it?) and other factors.

The Dispensing Provider, or the dispensing provider's MDD, updates the MMS database with the information that the patient has been issued the dispensed doses (9200). This information is available to Authorized Stakeholders, such as the patient, his Insurers, and/or his Physician. The MMS bills the patient and/or his Insurer for the dispensed dose(s) (6210).

If there was any problem with the Dispensing Provider that resulted in a failure to dispense the required medication, the patient is informed of where another Dispensing Provider is located that can dispense the prescription, the Dispensing Provider (or MDD) enters a service request for itself, and is marked as "unavailable" in the MMS database, so that other patients will not be sent there until the problem is corrected.

7.2 Example Process for a patient Taking a Scheduled Dose of Medication

FIG. 7 depicts an exemplary Process for a patient being alerted to take a scheduled dose of medication. At the time appropriate for a patient to take the dose, the patient's MMD alerts the patient that medication is due, using whatever mechanism has been set up for this (7110). The method used can involve an audible, visual, vibratory or other signal, or a combination of means, and the signal can be produced by the MMD itself, or through the use of another device or devices, such as a pager, cell phone, e-mail message, or alert to a Caregiver.

The patient authenticates to the MMD, acknowledges the alert, and checks the MMD's display to find which medication is to be taken. If the required dose has already been dispensed, the patient retrieves it. In some cases the patient can use the MMD's RFID or other reader device to verify that the proper package has been retrieved, while in others he can read a printed label and match the information with what the MMD is displaying. Once it has been verified that the proper medication has been retrieved, the patient takes it, then uses the MMD to record that the dose was taken (7140). The MMD records the time, the medication, and the patient ID information for transmission to the MMS at the next opportunity, or transmits the information immediately if possible (7150). The MMD then determines the proper time for the next dose, displays this information for the patient, and sets an alarm for that time, unless this was the final dose for the prescription. If the prescription is complete, the patient is so informed.

If the required dose has not already been dispensed (7130), the patient uses the MMD to locate a properly supplied Dispensing Provider (7132) and travels there to acquire the required dose (7134), and potentially additional doses if so authorized. The dose is taken and compliance reported as above (7140, 7150).

If the patient does not acknowledge the alert (7120), a Caregiver or Monitoring Service is alerted (7122), in case the patient is in distress. These can contact the patient by other means, or alert a First Responder, as appropriate (7124).

7.3 Patient Status Change Requires Prescription Adjustment

FIG. 8 depicts an exemplary Process for changing a patient's prescription due to a change in his physical state.

When it is requested by an Authenticated and Authorized Stakeholder, such as the patient's Physician, and is possible given the available hardware devices, the MMD uses patient-sensing devices to acquire data about the patient's current state (8110). This can be a regularly scheduled reading, or one commanded by the Authorized Stakeholder based on information provided by the patient or a Caregiver. The data is sent to the MMS database to be added to the patient's medical history records (8120), either immediately if possible or at the first opportunity if communication means are not available at the time. Alerts can be requested for sending when data is sent to the MMS database, or these can be filtered and only sent if the readings meet certain requirements (8130).

When the Physician reviews the sensor data, either due to an alert or in the normal course of events (8140), the Physician can determine that it is appropriate to adjust or change the patient's prescription (8150) in accordance with patient's current state and needs. In such a case, once the prescription change is accepted by the MMS, the MMS sends an alert to the patient's MMD (8160) to tell the patient about the change in prescription (e.g. dosage, medication or dose timing). The MMD updates its dose alert schedule appropriately (8170) and notifies the patient (8180).

If the patient has previously dispensed doses (8190), these are recorded as invalid, and potentially returnable (8195). The patient will not be told to take any of these doses, and in cases where an RFID or other mechanism for the MMD to use to identify a dose package exists, the MMD will display that the dose is invalid and not to be taken. In cases where the dose packaging is intact, it is possible to ensure that the dose has not experienced any adverse environmental conditions, and the dose is not custom-made for the particular patient, and where legislation does not prohibit it, the dose can be returnable for use by other patients.

Whether there are existing dispensed doses or not, the patient uses an appropriate Dispensing Provider to acquire required future doses and takes them as required by the updated prescription (8200), as depicted in FIGS. 6 and 7.

7.4 Patient Changes Designation of "Home" Dispensing Provider

FIG. 9 depicts an exemplary process for dealing with the situation where a patient changes their designated "home" Dispensing Provider from one device to another. Such a change can be a result of a number of causes, examples of which include, without limitation, a patient going on a short term trip, a patient moving into an assisted living facility, a patient changing jobs, or the removal of the patient's current "home" Dispensing Provider by the owning Stakeholder for business reasons.

A patient can use any properly equipped MMS Device to change the designation of their "home" Dispensing Provider (9110). This can include, without limitation, the existing Dispensing Provider, the patient's personal MMD, a web browser using a Stakeholder system's web interface for patient information update, a telephone call to the appropriate Stakeholder's customer service office, or any other means that the patient is authorized to use and that can authenticate the patient.

The patient's change is conveyed to the MMS Database (9120) immediately, or at a later time, as determined by the capabilities of the Communication and Networking System of the MMS. The patient's records are updated (9130), as are those of the particular Dispensing Provider (9140).

The MMS Database sends updated information to the patient's MMD (9150) so that the patient can be informed that the change has been accepted, and to the particular Dispensing Providers involved, which include at least the Dispensing Provider the patient has stopped designating as a "home" Dispensing Provider and the Dispensing Provider that the patient has newly designated as a "home" Dispensing Provider so that each may adjust their stocks of medication accordingly if necessary. Additional Dispensing Providers may be notified in some exemplary MMSs. For example, other Dispensing Providers in the vicinity of either the patient's prior "home" Dispensing Provider or the patient's new "home" Dispensing Provider, if the caching algorithm used by the MMS involves nearby Dispensing Providers and patient requirements in its calculations.

Each Dispensing Provider affected by the change re-calculates its proper stock of medications (9160) according to the caching algorithm in use and places orders for additional medications as required (9175), or notifies the appropriate aspects of the MMS that excess medications are being cached (9182), or does nothing, as required.

If a Dispensing Provider is caching excess medications (9180), a transfer of medications may be requested if this is appropriate given the business rules of the particular MMS and needs of other Dispensing Providers. Factors involved in this decision can include the cost of making the transfer, the cost of the medications involved, the likelihood that the medications will be needed in the immediate future based on past patterns of use, the availability of the particular medications from other sources for supplying the Dispensing Providers that require them, the expiration dates of the particular medications, or other factors as determined by those having skill in the art.

If a medication transfer is deemed to be proper, the MMS issues requests (9186) to the proper Stakeholders to remove the excess medications from the Dispensing Provider currently caching them, to transport the medications (9187) to another Dispensing Provider, or Dispensing Providers, that require them, and to install them in the receiving Dispensing Provider(s).

Both contributing Dispensing Provider and receiving Dispensing Provider(s) send updates to the MMS Database to specify their adjusted medication inventory contents (9188).

7.5 Monitored Packaging Methods
7.5.1 Loading Card Modules for MDD
7.5.1.1 Card Module with Same-Size Cells FIG. 10 depicts one example of a design for a loading module (10100) for the MDD, where each cell is of the same content size. Individual RAW product batch cells (10110) are blister-packaged into the module in rows and columns, with wire sensors to monitor the status of each row (10120) and column (10130). The status of each individual cell is also available as a machine-readable ID (10140). Machine-readable module perimeter defense status wires (10160) monitor the perimeter of the module for heat, moisture, and other adverse conditions. The module's unit ID and status is also available in a machine-readable format (10150). All of this status information is available at a contact (10170) at the edge of the module (10180), where the loading module interfaces with the MDD.

The Module itself can have both Contact and Non-Contact Machine Readable Status indicators not only for the entire module, but the individual cells as well. This type of Module (i.e. blister package "card", with foil overlay and same size cells) would be used where there is a limited variance in the dosing levels per body weight, and thus applicable for environments where the dosing would be likely to occur at something like a MIN~MAX of 10-"units" to 100-"units" in 10-"unit" steps. In some embodiments, the Module has ID for the module as a whole, Status for entire perimeter of the module, heat/moisture/shock/etc. Status, as well as "Opened/ Used" Status not only for the module itself, but also for each individual "cell". This concept can be applied to any type of item, such as a Fed-Ex package, due to the non-contact, machine-readable interfaces, allowing identification and status verification of medications in transit or prior to unpacking after delivery.

7.5.1.2 Card Module with Different-Size Cells

FIG. 11 depicts one example of a design for a loading module (11100) for the MDD, where the cells are of varying content size. Individual RAW product batch cells (11130) are blister-packaged into the module in rows and columns, with wire sensors to monitor the status of each row (11120) and column (11130). The status of each individual cell is also available as a machine-readable ID (11140). Machine-readable module perimeter defense status wires (11160) monitor the perimeter of the module for heat, moisture, and other adverse conditions. The module's unit ID and status is also available in a machine-readable format (11150). All of these modules are connected to a contact (11170) at the edge of the module (11180), where the loading module interfaces with the MDD.

The Module itself has both Contact and Non-Contact Machine Readable Status indicators for the entire module as a whole, and also for the individual cells. This type of Module (i.e. blister package "card", with foil overlay and different-size cells) can be used where there is a large variance in the dosing levels per body weight, and thus applicable for environments where the dosing would be likely to occur at something like a MIN~MAX of 10-"units" to 5000-"units" in 10-"unit" steps.

7.5.2 RFID Tagged Packaging

Modules, as described above, can benefit from using non-contact machine-readable status indicators such as RFID tags and barcode labels. RFID tags are particularly advantageous because they can be read by an RFID-reader equipped MMS device.

In some embodiments, it is desirable to have a duality of RFID, one to identify the packaging, and a second one to identify the status of the package (opened/not opened). Dual RFID tags slightly increase the cost of tagging medications, but add substantial benefits in the tracking of the medications and their status.

RFID tags can be used with standard commercial packaging mechanisms already in use today, specifically, they can be used in conjunction with standard baggies and envelopes to effect a tamper-detectable closure of these items. By using an RFID tag in this way, the RFID tag can identify if the bag or envelope has been opened or tampered with. A common reason for opening a bag or envelope is for a patient to take the contents of the bag or envelope.

7.5.3 RFID Tags

RFID tags can be used throughout the MMS to track the location, determine the type, and monitor the condition of various medications. For example, tags can be used in the Medication Tracking, Handling, and Dispensing subsystems of the Dispensing Provider provided Medication Dispensing Device, as shown in FIGS. 5*a*, 5*b*, and 5*c*, on both the raw materials used to make the medications, and on the dispensed medications themselves.

7.5.3.1 Single RFID Tags

FIGS. 12*a* and 12*b* depict exemplary RFID tags (12100 and 12200) that have a typical configuration of a chip (12120 and 12220) attached to an antenna (12110 and 12210). In a first embodiment using RFID tags, when the packaging is opened, perforations (12130 and 12230) rip the tag into two parts, separating the chip from its antenna, and making the tag unreadable. Once a tag is torn, the package is considered opened and the contents used. FIGS. 12a and 12b illustrate several potential ways of arranging an RFID chip, antenna, and perforation so as to effect the separation of tag and antenna when the tag is ripped.

7.5.3.2 Paired RFID Tags

FIG. 13 depicts an exemplary set of "paired" RFID tags (13100), each having a chip (13120 and 13150) and an antenna (13110 and 13140). In a second embodiment using RFID tags, when the packaging is opened, perforations (13130) tear apart and separate Tag A from Tag B. Tag A remains with the packaging, and Tag B is discarded. For example, Tag A can comprise the details of a medication dosage, and Tag B, by its presence or absence, can indicate whether the packaging has been opened.

FIG. 14 depicts a process for using "paired" RFID tags, such as those depicted in FIG. 13, to determine the state of a packaged medication. In step 14110, an MMS device scans for RFID tags. If no tags are present, the process terminates. If RFID tags are present (step 14120), the MMS device attempts to identify them (step 14130). If the tags do not match an existing type, the process terminates. If the tags are a known type, the MMS device compares them with a database of known paired tags (step 141 70). Alternatively, the MMS device can send the tag information to a Stakeholder, who compares them against a database of known paired tags. The MMS then can make a determination as to the state of the packaging based upon the presence or absence of complete pairs of tags. In FIG. 14, three example determinations are shown. In the first example, if both Tag A and Tag B are present (step 14160), then the packaging is intact (step 14170) and the medication inside is unused. If only Tag A (the medication dosage tag) is present (step 14164), the packaging has been opened and the medication is considered used (step 14174). If only Tag B (the tag that is supposed to be discarded upon opening the packaging) is present (step 14168), either the packaging has been opened or the paired tag has been tampered with (step 14178), and the package is recalled for further examination. The process then terminates.

8 CONCLUSION

Although various specific embodiments and examples have been described herein, those having ordinary skill in the art will understand that many different implementations of the invention can be achieved without departing from the spirit or scope of this disclosure. For example, the various systems, such as the MMS, MMD, MDD, and their related systems, can be configured to manage packaging and contents other than medication as well as the use of the contents other than patient compliance using the description herein and the knowledge of those having ordinary skill in the art.

9 BIBLIOGRAPHY

The following references are incorporated herein by reference in their entirety and for all purposes.

Beyth, R. J. and Shorr, R I. (1999). "Epidemiology of adverse drug reactions in the elderly by drug class." *Drugs Aging* 14(3): 231-9.

Braitstein, P., Justice, A., et al. (2006). "Hepatitis C co-infection is independently associated with decreased adherence to antiretroviral therapy in a population-based HIV cohort." *Aids* 20(3): 323-31.

Carballo, M. (2004). "[Adhesion to the antiretroviral treatment]." *Rev Enferm* 27(12): 18-24.

Collingsworth, S., Gould, D., et al. (1997). "patient self-administration of medication: a review of the literature." *Int J Nurs Stud* 34(4): 256-69.

Colombo, J. (1997). "Establishing pharmaceutical care services in an HIV clinic." *J Am Pharm Assoc (Wash)* NS37(5): 581-92; quiz 593-4.

Dennehy, C. E., Kishi, D. T., et al. (1996). "Drug-related illness in emergency department patients." *Am J Health Syst Pharm* 53(12): 1422-6.

Diaz, E., Neuse, E., et al. (2004). "Adherence to conventional and atypical antipsychotics after hospital discharge." *J Clin Psychiatry* 65(3): 354-60.

Erlen, J. A. and Sereika, S. M. (2006). "Fidelity to a 12-week structured medication adherence intervention in patients with HIV." *Nurs Res* 55(2 Suppl): S17-22.

Farabee, D. and Shen, H. (2004). "Antipsychotic medication adherence, cocaine use, and recidivism among a parolee sample." *Behav Sci Law* 22(4): 467-76.

Garcia Popa-Lisseanu, M. G., Greisinger, A., et al. (2005). "Determinants of treatment adherence in ethnically diverse, economically disadvantaged patients with rheumatic disease." *J Rheumatol* 32(5): 913-9.

Garcia, R., Schooley, R T., et al. (2003). "An adherence trilogy is essential for long-term HAART success." *Braz J Infect Dis* 7(5):307-14.

Gold, D. T. and Silverman, S. (2006). "Review of adherence to medications for the treatment of osteoporosis." *Curr Osteoporos Rep* 4(1): 21-7.

Goode, M., McMaugh, A., et al. (2003). "Adherence issues in children and adolescents receiving highly active antiretroviral therapy." *AIDS Care* 15(3): 403-8.

Halkitis, P. N., Kutnick, A. H., et al. (2005). "The social realities of adherence to protease inhibitor regimens: substance use, health care and psychological states." *J Health Psychol* 10(4): 545-58.

Hausman, A. (2001). "Taking your medicine: relational steps to improving patient compliance." Health Mark Q 19(2): 49-71.

Herrmann, J. M. and Gaus, E. (1981). "[The clinical significance of compliance]." Schweiz Med Wochenschr 111(51): 1998-2005.

Jay, S., Litt, I. F., et al. (1984). "Compliance with therapeutic regimens." *J Adolesc Health Care* 5(2): 124-36.

Kalsekar, I. D., Madhavan, S. S., et al. (2006). "Depression in patients with type 2 diabetes: impact on adherence to oral hypoglycemic agents." *Ann Pharmacother* 40(4): 605-11.

Kubesova, H., Holik, J., et al. (2006). "[Drug consumption and risks of polypharmacotherapy in elderly population]." *Cas Lek Cesk* 145(9): 708-11.

Mishra, P., Hansen, E. H., et al. (2006). "Adherence is associated with the quality of professional-patient interaction in Directly Observed Treatment Short-course, DOTS." *patient Educ Couns* 63(1-2): 29-37.

Nakonezny, P. A. and Byerly, M. J. (2006). "Electronically MMS adherence in outpatients with schizophrenia or schizoaffective disorder: a comparison of first- vs. second-generation antipsychotics." *Schizophr Res* 82(1): 107-14.

Nies, A. S. (1975). "Adverse reactions and interactions limiting the use of antihypertensive drugs." *Am J Med* 58(4): 495-503.

Nischal, K. C., Khopkar, U., et al. (2005). "Improving adherence to antiretroviral therapy." *Indian J Dermatol Venereol Leprol* 71(5): 316-20.

Peck, C. L. and King, N. J. (1982). "Increasing patient compliance with prescriptions." *Jama* 248(21): 2874-8.

Schafer, L. C., Glasgow, R. E., et al. (1983). "Adherence to IDDM regimens: relationship to psychosocial variables and metabolic control." *Diabetes Care* 6(5): 493-8.

Shope, J. T. (1988). "Compliance in children and adults: review of studies." *Epilepsy Res Suppl* 1: 23-47.

Slama, L., Le Camus, C., et al. (2006). "[Adherence to antiretroviral therapy during HIV infection, a multidisciplinary approach]." *Med Mal Infect* 36(1): 16-26.

Sung, J. C., Nichol, M. B., et al. (1998). "Factors affecting patient compliance with antihyperlipidemic medications in an HMO population." *Am J Manag Care* 4(10): 1421-30.

Tamblyn, R. (1996). "Medication use in seniors: challenges and solutions." *Therapie* 51(3): 269-82.

Tollefson, G. D. (1993). "Adverse drug reactions/interactions in maintenance therapy." *J Clin Psychiatry* 54 Suppl: 48-58; discussion 59-60.

Vrijens, B. and Goetghebeur, E. (1997). "Comparing compliance patterns between randomized treatments." *Control Clin Trials* 18(3): 187-203.

Waterhouse, D. M., Calzone, K. A., et al. (1993). "Adherence to oral tamoxifen: a comparison of patient self-report, pill counts, and microelectronic monitoring." *J Clin Oncol* 11(6): 1189-97.

Williams, A. (1997). "Antiretroviral therapy: factors associated with adherence." *J Assoc Nurses AIDS Care* 8 Suppl: 18-23.

Zaghloul, S. S., Cunliffe, W. J., et al. (2005). "Objective assessment of compliance with treatments in acne." *Br J Dermatol* 152(5): 1015-21.

Zaghloul, S. S. and Goodfield, M. J. (2004). "Objective assessment of compliance with psoriasis treatment." *Arch Dermatol* 140(4): 408-14.

What is claimed:

1. A method for monitoring patient medication compliance, comprising: providing a medication management system (MMS) for said patient and additional patient care stakeholders, said medication management system including at least a radiofrequency identification (RFID) scanner, a medication management database, and a medication dispensing device (MMD) configured to combine disparate medications into one or more pills and dispense said one or more pills to a patient; providing a package containing said one or more pills, said package including at least first and second paired active RFID tags arranged in said package such that both said first and second paired active RFID tags remain active after opening said package; monitoring the status of said first and second paired active RFID tags using said MMS; detecting that one of said first and second paired active RFID tags is absent; determining that said package has been opened; interfacing with at least one patient state sensor, obtaining patient state data, and relaying said patient state data to said MMS; updating said medication management database; and alerting at least one of said patient care stakeholders.

2. The method of claim 1, further comprising: configuring said first RFID tag to have at least two portions, wherein one portion is a perforated portion; and arranging said first RFID tag in said package such that opening said package is effective to separate one of said first and second paired active RFID tags from said package.

3. The method of claim 2, wherein one of said first and second paired active RFID tags is in one of said two portions and the other of said first and second paired active RFID tags is in the other of said two portions.

4. The method of claim 1, wherein said second RFID tag is arranged in said package such that said second RFID remains in said package after said package in opened.

5. The method of claim 1, further comprising storing an indicator of the relationship between said package and said first and second paired active RFID tags in a database.

6. The method of claim 5, further comprising storing said status of said package in a database.

7. The method of claim 6, further comprising defining said status of said package to opened upon said detecting that one of said first and second paired active RFID tags is detached from said package.

8. The method of claim 5, further comprising providing a database including status indicators for said first and second RFID tags.

9. The method of claim 5, further comprising providing a package status indicator derived said status indicators for said first and second RFID tags.

10. The method of claim 9, further comprising setting said status indicator to unopened if said first and said second RFID tags are determined to be attached to said package.

11. The method of claim 9, further comprising settings aid status indicator to damaged if said first RFID tag is determined to be operative and said second RFID tags is determined to be inoperative.

12. A system for monitoring the status of patient medication compliance, comprising:
  a. a medication management system (MMS) for said patient and additional patient care stakeholders, said medication management system including at least a radiofrequency identification (RFID) scanner and an medication management database; and said MMS being configured to interface with at least one patient state sensor, obtain patient state data, and relay said patient state data to said MMS, and alert a patient care stakeholder in response to a signal from said RFID scanner the one of said paired RFID tags is absent; and
  b. a medication dispensing device (MMD) configured to combine disparate medications into one or more pills and dispense said one or more pills to a patient; and
  c. a package containing said one or more pills, said package including first and second paired active RFID tags, said first and second paired active RFID tags being arranged such that both said first and second paired active RFID tags remain operative after opening said package.

13. The system of claim 12, further comprising an entry for the status of said package, wherein said status of said package is dependent at least in part on the statuses of said first and said second RFID tags.

14. The system of claim 12, wherein said second RFID tag is configured to store information about the contents of said package.

15. The system of claim 14, wherein said contents of said package is a medication, and said information includes patient dosing information for said medication.

* * * * *